(12) United States Patent
Van Gestel et al.

(10) Patent No.: US 7,498,343 B2
(45) Date of Patent: Mar. 3, 2009

(54) MYCOBACTERIAL INHIBITORS

(75) Inventors: Jozef Frans Elisabetha Van Gestel, Beerse (BE); Jérôme Emile Georges Guillemont, Val de Reuil Cedex (FR); Marc Gaston Venet, Le Mans (FR); Hervé Jean Joseph Poignet, Issy-les-Moulineaux Cedex 9 (FR); Laurence Françoise Bernadette Decrane, Val de Reuil Cedex (FR); Daniel F. J. Vernier, Val de Reuil Cedex (FR); Frank Christopher Odds, Drumoak (GB)

(73) Assignee: Janssen Pharmaceutica N.V., Beerse (BE)

( * ) Notice: Subject to any disclaimer, the term of this patent is extended or adjusted under 35 U.S.C. 154(b) by 442 days.

(21) Appl. No.: 11/007,026

(22) Filed: Dec. 8, 2004

(65) Prior Publication Data

US 2005/0148581 A1    Jul. 7, 2005

Related U.S. Application Data

(63) Continuation-in-part of application No. PCT/EP03/50322, filed on Jul. 18, 2003.

(60) Provisional application No. 60/398,711, filed on Jul. 25, 2002.

(51) Int. Cl.
*A61K 31/44* (2006.01)
*C07D 215/38* (2006.01)

(52) U.S. Cl. ................ 514/312; 514/311; 514/314; 546/153; 546/156

(58) Field of Classification Search ............. 514/227, 514/311, 312, 314; 546/156, 153
See application file for complete search history.

(56) References Cited

U.S. PATENT DOCUMENTS

2006/0142279 A1* 6/2006 Andries et al. ........... 514/227.8
2006/0281741 A1* 12/2006 Andries et al. ........... 514/227.8

OTHER PUBLICATIONS

Andries, Koen; A Diarylquinoline Drug Active on the ATP Synthase of *Mycobacterium tuberculosis*, Science vol. 307 Jan. 14, 2005 pp. 223-227.

* cited by examiner

Primary Examiner—D. Margaret Seaman
(74) Attorney, Agent, or Firm—John Harbour

(57) ABSTRACT

The present invention relates to novel substituted quinoline derivatives according to the general Formula (Ia) or the general Formula (Ib)

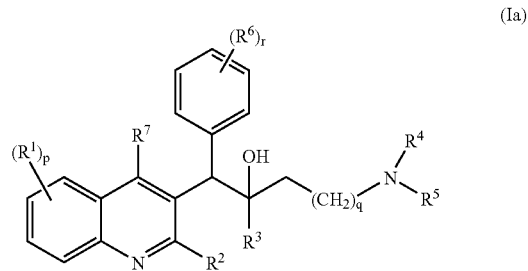

(Ia)

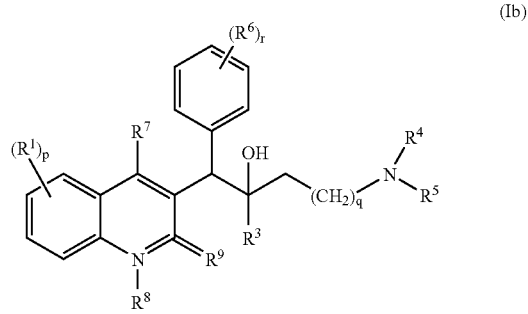

(Ib)

the pharmaceutically acceptable acid or base addition salts thereof, the stereochemically isomeric forms thereof, the tautomeric forms thereof and the N-oxide forms thereof. The claimed compounds are useful for the treatment of mycobacterial diseases, particularly those diseases caused by pathogenic mycobacteria such as *Mycobacterium tuberculosis, M. bovis, M. avium* and *M. marinum*. In particular, compounds are claimed in which, independently from each other, $R^1$ is bromo, p=1, $R^2$ is alkyloxy, $R^3$ is optionally substituted naphthyl or phenyl, q=1, $R^4$ and $R^5$ each independently are hydrogen, methyl or ethyl, $R^6$ is hydrogen, r is equal to 0 or 1 and $R^7$ is hydrogen. Also claimed is a composition comprising a pharmaceutically acceptable carrier and, as active ingredient, a therapeutically effective amount of the claimed compounds, the use of the claimed compounds or compositions for the manufacture of a medicament for the treatment of mycobacterial diseases and a process for preparing the claimed compounds.

24 Claims, No Drawings

MYCOBACTERIAL INHIBITORS

This application is a continuation in part of application PCT/EP03/50322, dated Jul. 18, 2003, which claims the benefit of priority of U.S. application 60/398,711, dated Jul. 25, 2002. The complete disclosures of the aforementioned related U.S. patent applications are hereby incorporated herein by reference for all purposes.

The present invention relates to novel substituted quinoline derivatives useful for the treatment of mycobacterial diseases, particularly those diseases caused by pathogenic mycobacteria such as *Mycobacterium tuberculosis, M. bovis, M. avium* and *M. marinum*.

BACKGROUND OF THE INVENTION

*Mycobacterium tuberculosis* is the causative agent of tuberculosis (TB), a serious and potentially fatal infection with a world-wide distribution. Estimates from the World Health Organization indicate that more than 8 million people contract TB each year, and 2 million people die from tuberculosis yearly. In the last decade, TB cases have grown 20% worldwide with the highest burden in the most impoverished communities. If these trends continue, TB incidence will increase by 41% in the next twenty years. Fifty years since the introduction of an effective chemotherapy, TB remains after AIDS, the leading infectious cause of adult mortality in the world. Complicating the TB epidemic is the rising tide of multi-drug-resistant strains, and the deadly symbiosis with HIV. People who are HIV-positive and infected with TB are 30 times more likely to develop active TB than people who are HIV-negative and TB is responsible for the death of one out of every three people with HIV/AIDS worldwide.

Existing approaches to treatment of tuberculosis all involve the combination of multiple agents. For example, the regimen recommended by the U.S. Public Health Service is a combination of isoniazid, rifampicin and pyrazinamide for two months, followed by isoniazid and rifampicin alone for a further four months. These drugs are continued for a further seven months in patients infected with HIV. For patients infected with multi-drug resistant strains of *M. tuberculosis*, agents such as ethambutol, streptomycin, kanamycin, amikacin, capreomycin, ethionamide, cycloserine, ciprofoxacin and ofloxacin are added to the combination therapies. There exists no single agent that is effective in the clinical treatment of tuberculosis, nor any combination of agents that offers the possibility of therapy of less than six months' duration.

There is a high medical need for new drugs that improve current treatment by enabling regimens that facilitate patient and provider compliance. Shorter regimens and those that require less supervision are the best way to achieve this. Most of the benefit from treatment comes in the first 2 months, during the intensive, or bactericidal, phase when four drugs are given together; the bacterial burden is greatly reduced, and patients become noninfectious. The 4- to 6-month continuation, or sterilizing, phase is required to eliminate persisting bacilli and to minimize the risk of relapse. A potent sterilizing drug that shortens treatment to 2 months or less would be extremely beneficial. Drugs that facilitate compliance by requiring less intensive supervision also are needed. Obviously, a compound that reduces both the total length of treatment and the frequency of drug administration would provide the greatest benefit.

Complicating the TB epidemic is the increasing incidence of multi-drug-resistant strains or MDR-TB. Up to four percent of all cases worldwide are considered MDR-TB—those resistant to the most effective drugs of the four-drug standard, isoniazid and rifampin. MDR-TB is lethal when untreated and can not be adequately treated through the standard therapy, so treatment requires up to 2 years of "second-line" drugs. These drugs are often toxic, expensive and marginally effective. In the absence of an effective therapy, infectious MDR-TB patients continue to spread the disease, producing new infections with MDR-TB strains. There is a high medical need for a new drug with a new mechanism of action, which is likely to demonstrate activity against MDR strains.

The purpose of the present invention is to provide novel compounds, in particular substituted quinoline derivatives, having the property of inhibiting growth of mycobacteria and therefore useful for the treatment of mycobacterial diseases, particularly those diseases caused by pathogenic mycobacteria such as *Mycobacterium tuberculosis, M. bovis, M. avium* and *M. marinum*.

Substituted quinolines were already disclosed in U.S. Pat. No. 5,965,572 (The United States of America) for treating antibiotic resistant infections and in WO 00/34265 to inhibit the growth of bacterial microorganisms. None of these publications disclose the substituted quinoline derivatives according to our invention.

SUMMARY OF THE INVENTION

The present invention relates to novel substituted quinoline derivatives according to Formula (Ia) or Formula (Ib)

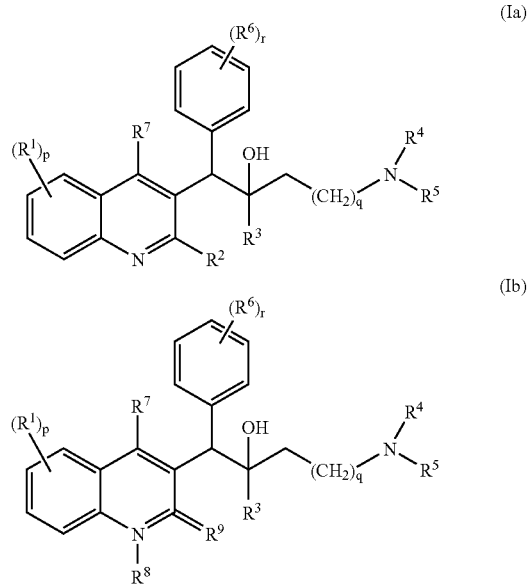

the pharmaceutically acceptable acid or base addition salts thereof, the stereochemically isomeric forms thereof, the tautomeric forms thereof and the N-oxide forms thereof, wherein:

$R^1$ is hydrogen, halo, haloalkyl, cyano, hydroxy, Ar, Het, alkyl, alkyloxy, alkylthio, alkyloxyalkyl, alkylthioalkyl, Ar-alkyl or di(Ar)alkyl;

p is an integer equal to zero, 1, 2, 3 or 4;

$R^2$ is hydrogen, hydroxy, thio, alkyloxy, alkyloxyalkyloxy, alkylthio, mono or di(alkyl)amino or a radical of formula

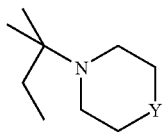

wherein Y is $CH_2$, O, S, NH or N-alkyl;
$R^3$ is alkyl, Ar, Ar-alkyl, Het or Het-alkyl;
q is an integer equal to zero, 1, 2, 3 or 4;
$R^4$ and $R^5$ each independently are hydrogen, alkyl or benzyl; or
$R^4$ and $R^5$ together and including the N to which they are attached may form a radical selected from the group of pyrrolidinyl, 2H-pyrrolyl, 2-pyrrolinyl, 3-pyrrolinyl, pyrrolyl, imidazolidinyl, pyrazolidinyl, 2-imidazolinyl, 2-pyrazolinyl, imidazolyl, pyrazolyl, triazolyl, piperidinyl, pyridinyl, piperazinyl, imidazolidinyl, pyridazinyl, pyrimidinyl, pyrazinyl, triazinyl, morpholinyl and thiomorpholinyl, optionally substituted with alkyl, halo, haloalkyl, hydroxy, alkyloxy, amino, mono- or dialkylamino, alkylthio, alkyloxyalkyl, alkylthioalkyl and pyrimidinyl;
$R^6$ is hydrogen, halo, haloalkyl, hydroxy, Ar, alkyl, alkyloxy, alkylthio, alkyloxyalkyl, alkylthioalkyl, Ar-alkyl or di(Ar)alkyl; or
two vicinal $R^6$ radicals may be taken together to form a bivalent radical of formula —CH═CH—CH═CH—;
r is an integer equal to 0, 1, 2, 3, 4 or 5; and
$R^7$ is hydrogen, alkyl, Ar or Het;
$R^8$ is hydrogen or alkyl;
$R^9$ is oxo; or
$R^8$ and $R^9$ together form the radical ═N—CH═CH—.
alkyl is a straight or branched saturated hydrocarbon radical having from 1 to 6 carbon atoms; or is a cyclic saturated hydrocarbon radical having from 3 to 6 carbon atoms; or is a cyclic saturated hydrocarbon radical having from 3 to 6 carbon atoms attached to a straight or branched saturated hydrocarbon radical having from 1 to 6 carbon atoms; wherein each carbon atom can be optionally substituted with halo, hydroxy, alkyloxy or oxo;
Ar is a homocycle selected from the group of phenyl, naphthyl, acenaphthyl, tetrahydronaphthyl, each optionally substituted with 1, 2 or 3 substituents, each substituent independently selected from the group of hydroxy, halo, cyano, nitro, amino, mono- or dialkylamino, alkyl, haloalkyl, alkyloxy, haloalkyloxy, carboxyl, alkyloxycarbonyl, aminocarbonyl, morpholinyl and mono- or dialkylaminocarbonyl;
Het is a monocyclic heterocycle selected from the group of N-phenoxypiperidinyl, pyrrolyl, pyrazolyl, imidazolyl, furanyl, thienyl, oxazolyl, isoxazolyl, thiazolyl, isothiazolyl, pyridinyl, pyrimidinyl, pyrazinyl and pyridazinyl; or a bicyclic heterocycle selected from the group of quinolinyl, quinoxalinyl, indolyl, benzimidazolyl, benzoxazolyl, benzisoxazolyl, benzothiazolyl, benzisothiazolyl, benzofuranyl, benzothienyl, 2,3-dihydrobenzo[1,4]dioxinyl or benzo[1,3]dioxolyl; each monocyclic and bicyclic heterocycle may optionally be substituted on a carbon atom with 1, 2 or 3 substituents selected from the group of halo, hydroxy, alkyl or alkyloxy;
halo is a substituent selected from the group of fluoro, chloro, bromo and iodo and
haloalkyl is a straight or branched saturated hydrocarbon radical having from 1 to 6 carbon atoms or a cyclic saturated hydrocarbon radical having from 3 to 6 carbon atoms, wherein one or more carbon atoms are substituted with one or more halo-atoms.

The compounds according to Formula (Ia) and (Ib) are interrelated in that e.g. a compound according to Formula (Ib), with $R^9$ equal to oxo is the tautomeric equivalent of a compound according to Formula (Ia) with $R^2$ equal to hydroxy (keto-enol tautomerism).

DETAILED DESCRIPTION

In the framework of this application, alkyl is a straight or branched saturated hydrocarbon radical having from 1 to 6 carbon atoms; or is a cyclic saturated hydrocarbon radical having from 3 to 6 carbon atoms; or is a cyclic saturated hydrocarbon radical having from 3 to 6 carbon atoms attached to a straight or branched saturated hydrocarbon radical having from 1 to 6 carbon atoms; wherein each carbon atom can be optionally substituted with halo, hydroxy, alkyloxy or oxo.

Preferably, alkyl is methyl, ethyl or cyclohexylmethyl.

In the framework of this application, Ar is a homocycle selected from the group of phenyl, naphthyl, acenaphthyl, tetrahydronaphthyl, each optionally substituted with 1, 2 or 3 substituents, each substituent independently selected from the group of hydroxy, halo, cyano, nitro, amino, mono- or dialkylamino, alkyl, haloalkyl, alkyloxy, haloalkyloxy, carboxyl, alkyloxycarbonyl, aminocarbonyl, morpholinyl and mono- or dialkylaminocarbonyl. Preferably, Ar is naphthyl or phenyl, each optionally substituted with 1 or 2 halo substituents.

In the framework of this application, Het is a monocyclic heterocycle selected from the group of N-phenoxypiperidinyl, pyrrolyl, pyrazolyl, imidazolyl, furanyl, thienyl, oxazolyl, isoxazolyl, thiazolyl, isothiazolyl, pyridinyl, pyrimidinyl, pyrazinyl and pyridazinyl; or a bicyclic heterocycle selected from the group of quinolinyl, quinoxalinyl, indolyl, benzimidazolyl, benzoxazolyl, benzisoxazolyl, benzothiazolyl, benzisothiazolyl, benzofuranyl, benzothienyl, 2,3-dihydrobenzo[1,4]dioxinyl or benzo[1,3]dioxolyl; each monocyclic and bicyclic heterocycle may optionally be substituted on a carbon atom with 1, 2 or 3 substituents selected from the group of halo, hydroxy, alkyl or alkyloxy. Preferably, Het is thienyl.

In the framework of this application, halo is a substituent selected from the group of fluoro, chloro, bromo and iodo and haloalkyl is a straight or branched saturated hydrocarbon radical having from 1 to 6 carbon atoms or a cyclic saturated hydrocarbon radical having from 3 to 6 carbon atoms, wherein one or more carbonatoms are substituted with one or more halo-atoms. Preferably, halo is bromo, fluoro or chloro and preferably, haloalkyl is trifluoromethyl.

When two vicinal $R^6$ radicals are taken together to form a bivalent radical of formula —CH═CH—CH═CH—, this means that the two vicinal $R^6$ radicals form together with the phenyl ring to which they are attached a naphthyl.

Preferably, the invention relates to compounds of Formula (Ia) and (Ib) wherein:
$R^1$ is hydrogen, halo, cyano, Ar, Het, alkyl, and alkyloxy;
p is an integer equal to zero, 1, 2, 3 or 4;

$R^2$ is hydrogen, hydroxy, alkyloxy, alkyloxyalkyloxy, alkylthio or a radical of formula

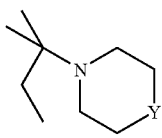

wherein Y is O;
$R^3$ is alkyl, Ar, Ar-alkyl or Het;
q is an integer equal to zero, 1, 2, or 3;
$R^4$ and $R^5$ each independently are hydrogen, alkyl or benzyl; or
$R^4$ and $R^5$ together and including the N to which they are attached may form a radical selected from the group of pyrrolidinyl, imidazolyl, triazolyl, piperidinyl, piperazinyl, pyrazinyl, morpholinyl and thiomorpholinyl, optionally substituted with alkyl and pyrimidinyl;
$R^6$ is hydrogen, halo or alkyl; or
two vicinal $R^6$ radicals may be taken together to form a bivalent radical of formula —CH=CH—CH=CH—;
r is an integer equal to 1; and
$R^7$ is hydrogen;
$R^8$ is hydrogen or alkyl;
$R^9$ is oxo; or
$R^8$ and $R^9$ together form the radical =N—CH=CH—.
alkyl is a straight or branched saturated hydrocarbon radical having from 1 to 6 carbon atoms; or is a cyclic saturated hydrocarbon radical having from 3 to 6 carbon atoms; or is a cyclic saturated hydrocarbon radical having from 3 to 6 carbon atoms attached to a straight or branched saturated hydrocarbon radical having from 1 to 6 carbon atoms; wherein each carbon atom can be optionally substituted with halo or hydroxy;
Ar is a homocycle selected from the group of phenyl, naphthyl, acenaphthyl, tetrahydronaphthyl, each optionally substituted with 1, 2 or 3 substituents, each substituent independently selected from the group of halo, haloalkyl, cyano, alkyloxy and morpholinyl;
Het is a monocyclic heterocycle selected from the group of N-phenoxypiperidinyl, furanyl, thienyl, pyridinyl, pyrimidinyl; or a bicyclic heterocycle selected from the group of benzothienyl, 2,3-dihydrobenzo[1,4]dioxinyl or benzo[1,3]-dioxolyl; each monocyclic and bicyclic heterocycle may optionally be substituted on a carbon atom with 1, 2 or 3 alkyl substituents; and
halo is a substituent selected from the group of fluoro, chloro and bromo.

For compounds according to either Formula (Ia) and (Ib), preferably, $R^1$ is hydrogen, halo, Ar, alkyl or alkyloxy. More preferably, $R^1$ is halo. Most preferably, $R^1$ is bromo.

Preferably, p is equal to 1.

Preferably, $R^2$ is hydrogen, alkyloxy or alkylthio. More preferably, $R^2$ is alkyloxy. Most preferably, $R^2$ is methyloxy.

Preferably, $R^3$ is naphthyl, phenyl or thienyl, each optionally substituted with 1 or 2 substituents, that substituent preferably being a halo or haloalkyl, most preferably being a halo. More preferably, $R^3$ is naphthyl or phenyl. Most preferably, $R^3$ is naphthyl.

Preferably, q is equal to zero, 1 or 2. More preferably, q is equal to 1.

Preferably, $R^4$ and $R^5$ each independently are hydrogen or alkyl, more preferably hydrogen, methyl or ethyl, most preferably methyl.

Preferably $R^4$ and $R^5$ together and including the N to which they are attached form a radical selected from the group of imidazolyl, triazolyl, piperidinyl, piperazinyl and thiomorpholinyl, optionally substituted with alkyl, halo, haloalkyl, hydroxy, alkyloxy, alkylthio, alkyloxyalkyl or alkylthioalkyl, preferably substituted with alkyl, most preferably substituted with methyl or ethyl.

Preferably, $R^6$ is hydrogen, alkyl or halo. Most preferably, $R^6$ is hydrogen. Preferably r is 0, 1 or 2.

Preferably, $R^7$ is hydrogen or methyl.

For compounds according to Formula (Ib) only, preferably, $R^8$ is alkyl, preferably methyl and $R^9$ is oxygen.

An interesting group of compounds are those compounds according to Formula (Ia), the pharmaceutically acceptable acid or base addition salts thereof, the stereochemically isomeric forms thereof, the tautomeric forms thereof and the N-oxide forms thereof, in which $R^1$ is hydrogen, halo, Ar, alkyl or alkyloxy, p=1, $R^2$ is hydrogen, alkyloxy or alkylthio, $R^3$ is naphthyl, phenyl or thienyl, each optionally substituted with 1 or 2 substituents selected from the group of halo and haloalkyl, q=0, 1, 2 or 3, $R^4$ and $R^5$ each independently are hydrogen or alkyl or $R^4$ and $R^5$ together and including the N to which they are attached form a radical selected from the group of imidazolyl, triazolyl, piperidinyl, piperazinyl and thiomorpholinyl, $R^6$ is hydrogen, alkyl or halo, r is equal to 0 or 1 and $R^7$ is hydrogen.

Preferably, the compound is:
1-(6-bromo-2-methoxy-quinolin-3-yl)-2-(3,5-difluoro-phenyl)$_4$-dimethylamino-1-phenyl-butan-2-ol;
1-(6-bromo-2-methoxy-quinolin-3-yl)-4-dimethylamino-2-naphthalen-1-yl-1-phenyl-butan-2-ol;
1-(6-bromo-2-methoxy-quinolin-3-yl)-2-(2,5-difluoro-phenyl)$_4$-dimethylamino-1-phenyl-butan-2-ol;
1-(6-bromo-2-methoxy-quinolin-3-yl)-2-(2,3-difluoro-phenyl)$_4$-dimethylamino-1-phenyl-butan-2-ol;
1-(6-bromo-2-methoxy-quinolin-3-yl)-4-dimethylamino-2-(2-fluoro-phenyl)-1-phenyl-butan-2-ol;
1-(6-bromo-2-methoxy-quinolin-3-yl)-4-dimethylamino-2-naphthalen-1-yl-1-p-tolyl-butan-2-ol;
1-(6-bromo-2-methoxy-quinolin-3-yl)-4-methylamino-2-naphthalen-1-yl-1-phenyl-butan-2-ol; and
1-(6-bromo-2-methoxy-quinolin-3-yl)-4-dimethylamino-2-(3-fluoro-phenyl)-1-phenyl-butan-2-ol, the pharmaceutically acceptable acid or base addition salts thereof, the stereochemically isomeric forms thereof, the tautomeric forms thereof and the N-oxide forms thereof.

Particularly preferred is 1-(6-bromo-2-methoxy-quinolin-3-yl)-4-dimethylamino-2-naphthalen-1-yl-1-phenyl-butan-2-ol; a pharmaceutically acceptable acid or base addition salt thereof, a stereochemically isomeric form thereof, and a N-oxide form thereof. Most preferred is (1R,2S) 1-(6-bromo-2-methoxy-quinolin-3-yl)-4-dimethylamino-2-naphthalen-1-yl-1-phenyl-butan-2-ol; a pharmaceutically acceptable acid or base addition salt thereof or a N-oxide form thereof.

The pharmaceutically acceptable acid addition salts are defined to comprise the therapeutically active non-toxic acid addition salt forms which the compounds according to either Formula (Ia) and (Ib) are able to form. Said acid addition salts can be obtained by treating the base form of the compounds according to either Formula (Ia) and (Ib) with appropriate acids, for example inorganic acids, for example hydrohalic acid, in particular hydrochloric acid, hydrobromic acid, sulfuric acid, nitric acid and phosphoric acid; organic acids, for example acetic acid, hydroxyacetic acid, propanoic acid, lactic acid, pyruvic acid, oxalic acid, malonic acid, succinic acid, maleic acid, fumaric acid, malic acid, tartaric acid, citric acid, methanesulfonic acid, ethanesulfonic acid, benzenesulfonic acid, p-toluenesulfonic acid, cyclamic acid, salicyclic acid, p-aminosalicylic acid and pamoic acid.

The compounds according to either Formula (Ia) and (Ib) containing acidic protons may also be converted into their therapeutically active non-toxic base addition salt forms by treatment with appropriate organic and inorganic bases. Appropriate base salts forms comprise, for example, the ammonium salts, the alkaline and earth alkaline metal salts, in particular lithium, sodium, potassium, magnesium and calcium salts, salts with organic bases, e.g. the benzathine, N-methyl-D-glucamine, hybramine salts, and salts with amino acids, for example arginine and lysine.

Conversely, said acid or base addition salt forms can be converted into the free forms by treatment with an appropriate base or acid.

The term addition salt as used in the framework of this application also comprises the solvates which the compounds according to either Formula (Ia) and (Ib) as well as the salts thereof, are able to form. Such solvates are, for example, hydrates and alcoholates.

The term "stereochemically isomeric forms" as used herein defines all possible isomeric forms which the compounds of either Formula (Ia) and (Ib) may possess. Unless otherwise mentioned or indicated, the chemical designation of compounds denotes the mixture of all possible stereochemically isomeric forms, said mixtures containing all diastereomers and enantiomers of the basic molecular structure. More in particular, stereogenic centers may have the R- or S-configuration; substituents on bivalent cyclic (partially) saturated radicals may have either the cis- or trans-configuration. Stereochemically isomeric forms of the compounds of either Formula (Ia) and (Ib) are obviously intended to be embraced within the scope of this invention.

Following CAS-nomenclature conventions, when two stereogenic centers of known absolute configuration are present in a molecule, an R or S descriptor is assigned (based on Cahn-Ingold-Prelog sequence rule) to the lowest-numbered chiral center, the reference center. The configuration of the second stereogenic center is indicated using relative descriptors [R*,R*] or [R*,S*], where R* is always specified as the reference center and [R*,R*] indicates centers with the same chirality and [R*,S*] indicates centers of unlike chirality. For example, if the lowest-numbered chiral center in the molecule has an S configuration and the second center is R, the stereo descriptor would be specified as S-[R*,S*]. If "α" and "β" are used: the position of the highest priority substituent on the asymmetric carbon atom in the ring system having the lowest ring number, is arbitrarily always in the "α" position of the mean plane determined by the ring system. The position of the highest priority substituent on the other asymmetric carbon atom in the ring system relative to the position of the highest priority substituent on the reference atom is denominated "α", if it is on the same side of the mean plane determined by the ring system, or "β", if it is on the other side of the mean plane determined by the ring system.

Compounds of either Formula (Ia) and (Ib) and some of the intermediate compounds invariably have at least two stereogenic centers in their structure which may lead to at least 4 stereochemically different structures.

The tautomeric forms of the compounds of either Formula (Ia) and (Ib) are meant to comprise those compounds of either Formula (Ia) and (Ib) wherein e.g. an enol group is converted into a keto group (keto-enol tautomerism).

The N-oxide forms of the compounds according to either Formula (Ia) and (Ib) are meant to comprise those compounds of either Formula (Ia) and (Ib) wherein one or several nitrogen atoms are oxidized to the so-called N-oxide, particularly those N-oxides wherein the nitrogen of the amine radical is oxidized.

The compounds of either Formula (Ia) and (Ib) as prepared in the processes described below may be synthesized in the form of racemic mixtures of enantiomers which can be separated from one another following art-known resolution procedures. The racemic compounds of either Formula (Ia) and (Ib) may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of either Formula (Ia) and (Ib) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

The invention also comprises derivative compounds (usually called "pro-drugs") of the pharmacologically-active compounds according to the invention, which are degraded in vivo to yield the compounds according to the invention. Pro-drugs are usually (but not always) of lower potency at the target receptor than the compounds to which they are degraded Pro-drugs are particularly useful when the desired-compound has chemical or physical properties that make its administration difficult or inefficient. For example, the desired compound may be only poorly soluble, it may be poorly transported across the mucosal epithelium, or it may have an undesirably short plasma half-life. Further discussion on pro-drugs may be found in Stella, V. J. et al., "Prodrugs", *Drug Delivery Systems,* 1985, pp. 112-176, and *Drugs,* 1985, 29, pp. 455-473.

Pro-drugs forms of the pharmacologically-active compounds according to the invention will generally be compounds according to either Formula (Ia) and (Ib), the pharmaceutically acceptable acid or base addition salts thereof, the stereochemically isomeric forms thereof, the tautomeric forms thereof and the N-oxide forms thereof, having an acid group which is esterified or amidated. Included in such esterified acid groups are groups of the formula —COOR$^x$, where R$^x$ is a C$_{1-6}$alkyl, phenyl, benzyl or one of the following groups:

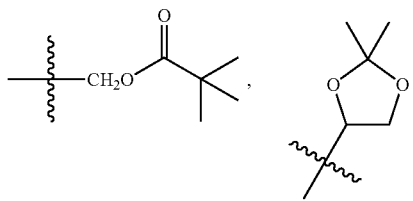

Amidated groups include groups of the formula —CONR$^y$R$^z$, wherein R$^y$ is H, C$_{1-6}$alkyl, phenyl or benzyl and R$^z$ is —OH, H, C$_{1-6}$alkyl, phenyl or benzyl.

Compounds according to the invention having an amino group may be derivatised with a ketone or an aldehyde such as formaldehyde to form a Mannich base. This base will hydrolyze with first order kinetics in aqueous solution.

The compounds according to the invention have surprisingly been shown to be suitable for the treatment of mycobacterial diseases, particularly those diseases caused by pathogenic mycobacteria such as *Mycobacterium tuberculosis*, *M. bovis*, *M. avium* and *M. marinum*. The present invention thus also relates to compounds of either Formula (Ia) and (Ib) as defined hereinabove, the pharmaceutically acceptable acid or base addition salts thereof, the stereochemically isomeric forms thereof, the tautomeric forms thereof and the N-oxide forms thereof, for use as a medicine.

The invention also relates to a composition comprising a pharmaceutically acceptable carrier and, as active ingredient, a therapeutically effective amount of a compound according to the invention. The compounds according to the invention may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, in particular, for administration orally or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, diluents, lubricants, binders, disintegrating agents and the like in the case of powders, pills, capsules and tablets. Because of their ease in administration, tablets and capsules represent the most advantageous oral dosage unit forms in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations which are intended to be converted, shortly before use, to liquid form preparations.

Depending on the mode of administration, the pharmaceutical composition will preferably comprise from 0.05 to 99% by weight, more preferably from 0.1 to 70% by weight of the active ingredient, and, from 1 to 99.95% by weight, more preferably from 30 to 99.9 weight % of a pharmaceutically acceptable carrier, all percentages being based on the total composition.

The pharmaceutical composition may additionally contain various other ingredients known in the art, for example, a lubricant, stabilising agent, buffering agent, emulsifying agent, viscosity-regulating agent, surfactant, preservative, flavouring or colorant.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof. The daily dosage of the compound according to the invention will, of course, vary with the compound employed, the mode of administration, the treatment desired and the mycobacterial disease indicated. However, in general, satisfactory results will be obtained when the compound according to the invention is administered at a daily dosage not exceeding 1 gram, e.g. in the range from 10 to 50 mg/kg body weight.

Further, the present invention also relates to the use of a compound of either Formula (Ia) and (Ib), the pharmaceutically acceptable acid or base addition salts thereof, the stereochemically isomeric forms thereof, the tautomeric forms thereof and the N-oxide forms thereof, as well as any of the aforementioned pharmaceutical compositions thereof for the manufacture of a medicament for the treatment of mycobacterial diseases.

Accordingly, in another aspect, the invention provides a method of treating a patient suffering from, or at risk of, a mycobacterial disease, which comprises administering to the patient a therapeutically effective amount of a compound or pharmaceutical composition according to the invention.

General Preparation

The compounds according to the invention can generally be prepared by a succession of steps, each of which is known to the skilled person.

In particular, the compounds according to Formula (Ia) can be prepared by reacting an intermediate compound of Formula (II) with an intermediate compound of Formula (III) according to the following reaction scheme (1):

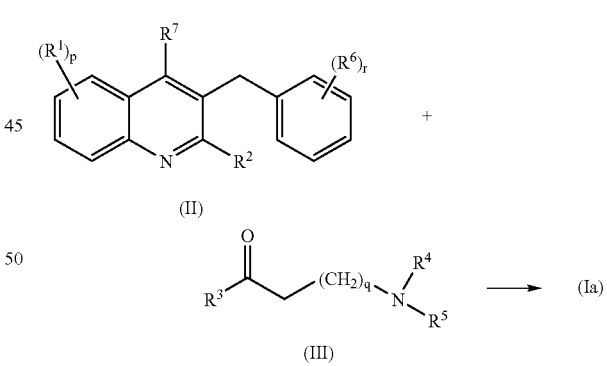

using BuLi in a mixture of DIPA and THF, wherein all variables are defined as in Formula (Ia). Stirring may enhance the rate of the reaction. The reaction may conveniently be carried out at a temperature ranging between −20 and −70° C.

The starting materials and the intermediate compounds of Formula (II) and (III) are compounds that are either commercially available or may be prepared according to conventional reaction procedures generally known in the art. For example, intermediate compounds of Formula (II-a) may be prepared according to the following reaction scheme (2):

Scheme 2

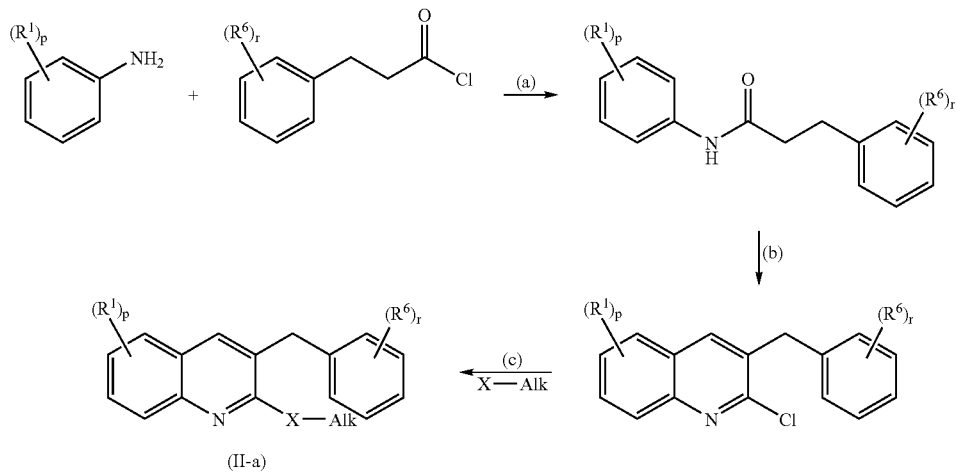

wherein all variables are defined as in Formula (Ia) and (Ib). Reaction scheme (2) comprises step (a) in which an appropriately substituted aniline is reacted with an appropriate acylchloride such as 3-phenylpropionyl chloride, 3-fluorobenzenepropionyl chloride or p-chlorobenzenepropionyl chloride, in the presence of a suitable base, such as triethylamine and a suitable reaction-inert solvent, such as methylene chloride or ethylene dichloride. The reaction may conveniently be carried out at a temperature ranging between room temperature and reflux temperature. In a next step (b) the adduct obtained in step (a) is reacted with phosphoryl chloride ($POCl_3$) in the presence of N,N-dimethylformamide (Vilsmeier-Haack formylation followed by cyclization). The reaction may conveniently be carried out at a temperature ranging between room temperature and reflux temperature. In a next step (c) a specific $R^3$-group, wherein $R^3$ is an alkyloxy or alkylthio radical is introduced by reacting the intermediate compound obtained in step (b) with a compound X-Alk, wherein X=S or O and Alk is an alkylgroup as defined in Formula (Ia) and (Ib).

Intermediate compounds according to Formula (II-b) may be prepared according to the following reaction scheme (3), wherein in a first step (a) a substituted indole-2,3-dione is reacted with a substituted 3-phenylpropionaldehyde in the presence of a suitable base such as sodium hydroxide (Pfitzinger reaction), after which the carboxylic acid compound in a next step (b) is decarboxylated at high temperature in the presence of a suitable reaction-inert solvent usch as diphenylether.

Scheme 3

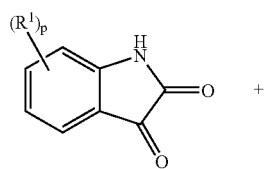

It is evident that in the foregoing and in the following reactions, the reaction products may be isolated from the reaction medium and, if necessary, further purified according to methodologies generally known in the art, such as extraction, crystallization and chromatography. It is further evident that reaction products that exist in more than one enantiomeric form, may be isolated from their mixture by known techniques, in particular preparative chromatography, such as preparative HPLC. Typically, compounds of Formula (Ia) and (Ib) may be separated into their isomeric forms.

The intermediate compounds of Formula (III) are compounds that are either commercially available or may be prepared according to conventional reaction procedures generally known in the art. For example, intermediate compounds of Formula (III-a) in which $R^3$ is Ar substituted with s substituents $R^{10}$, wherein each $R^{10}$ is independently selected from the group of hydroxy, halo, cyano, nitro, amino, mono- or dialkylamino, alkyl, haloalkyl, alkyloxy, haloalkyloxy, carboxyl, alkyloxycarbonyl, aminocarbonyl, morpholinyl and mono- or dialkylaminocarbonyl ans s is an integer equal to zero, 1, 2 or 3, may be prepared according to the following reaction scheme (4):

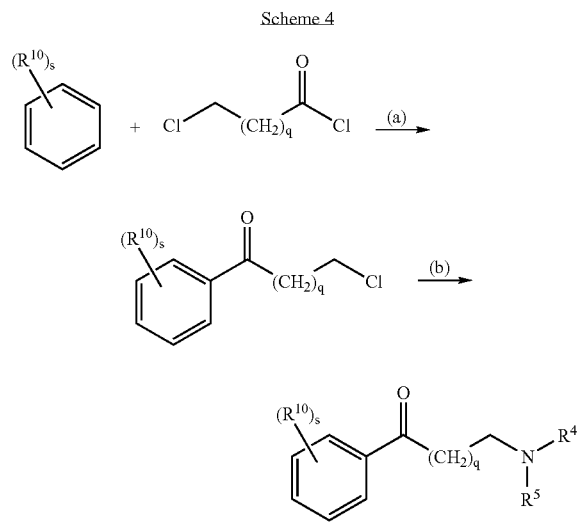

Reaction scheme (4) comprises step (a) in which an appropriately substituted phenyl is reacted by Friedel-Craft reaction with an appropriate acylchloride such as 3-chloropropionyl chloride or 4-chlorobutyryl chloride, in the presence of a suitable Lewis acid, such as $AlCl_3$, $FeCl_3$, $SnCl_4$, $TiCl_4$ or $ZnCl_2$ and a suitable reaction-inert solvent, such as methylene chloride or ethylene dichloride. The reaction may conveniently be carried out at a temperature ranging between room temperature and reflux temperature. In a next step (b) an amino group (—$NR_4R_5$) is introduced by reacting the intermediate compound obtained in step (a) with a primary or secondary amine.

The following examples illustrate the present invention without being limited thereto.

Experimental Part

Of some compounds the absolute stereochemical configuration of the stereogenic carbon atom(s) therein was not experimentally determined. In those cases the stereochemically isomeric form which was first isolated is designated as "A" and the second as "B", without further reference to the actual stereochemical configuration. However, said "A" and "B" isomeric forms can be unambiguously characterized by a person skilled in the art, using art-known methods such as, for example, X-ray diffraction. The isolation method is described in detail below.

In case "A" and "B" are stereoisomeric mixtures, they can be further separated whereby the respective first fractions isolated are designated "A1" and "B1" and the second as "A2" and "B2", without further reference to the actual stereochemical configuration.

Hereinafter, "DMF" is defined as N,N-dimethylformamide, "DIPE" is defined as diisopropyl ether, "THF" is defined as tetrahydrofuran.

A. Preparation of the Intermediate Compounds

EXAMPLE A1

Preparation of intermediate compound 1

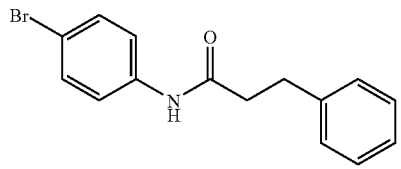

Benzenepropanoylchloride (0.488 mol) was added dropwise at room temperature to a solution of 4-bromobenzenamine (0.407 mol) in $Et_3N$ (70 ml) and $CH_2Cl_2$ (700 ml) and the mixture was stirred at room temperature overnight. The mixture was poured out into water and concentrated $NH_4OH$, and extracted with $CH_2Cl_2$. The organic layer was dried ($MgSO_4$), filtered, and the solvent was evaporated. The residue was crystallized from diethyl ether. The residue (119.67 g) was taken up in $CH_2Cl_2$ and washed with HCl 1N. The organic layer was dried ($MgSO_4$), filtered, and the solvent was evaporated. Yielding: 107.67 g of intermediate compound 1.

Preparation of intermediate compound 9

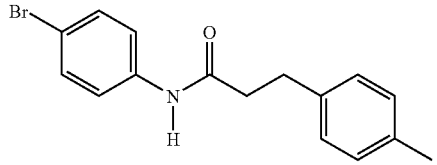

Accordingly, intermediate compound 9 was prepared in the same way as intermediate compound 1 but using 4-methylbenzenepropanoylchloride.

EXAMPLE A2

Preparation of intermediate compound 2

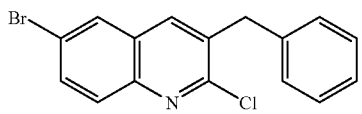

The reaction was carried out twice. $POCl_3$ (1.225 mol) was added dropwise at 10° C. to DMF (0.525 mol). Then intermediate compound 1 (prepared according A1) (0.175 mol) was added at room temperature. The mixture was stirred overnight at 80° C., poured out on ice and extracted with $CH_2Cl_2$. The organic layer was dried ($MgSO_4$), filtered, and the solvent was evaporated. The product was used without further purification. Yielding: (77.62 g; Yield=67%).

Preparation of intermediate compound 10

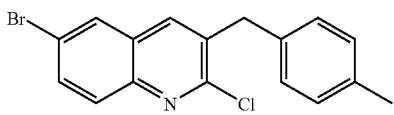

Accordingly, intermediate compound 10 was prepared in the same way as intermediate compound 2, starting from intermediate compound 9 (prepared according to A1).

EXAMPLE A3

Preparation of intermediate compound 3

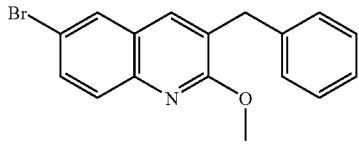

A mixture of intermediate compound 2 (prepared according to A2) (0.233 mol) in CH$_3$ONa (30%) in methanol (222.32 ml) and methanol (776 ml) was stirred and refluxed overnight, then poured out on ice and extracted with CH$_2$Cl$_2$. The organic layer was separated, dried (MgSO$_4$), filtered and the solvent was evaporated. The residue was purified by column chromatography over silica gel (eluent: CH$_2$Cl$_2$/cyclohexane 20/80 and then 100/0; 20-45 μm). The pure fractions were collected and the solvent was evaporated. Yielding: 25 g of intermediate compound 3 (Yield=33%; mp. 84° C.) as a white powder.

Preparation of intermediate compound 11

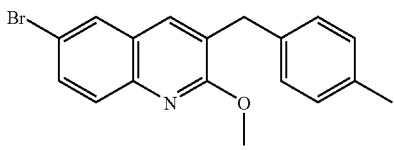

Accordingly, intermediate compound 11 was prepared in the same way as intermediate compound 3, starting from intermediate compound 10 (prepared according to A2).

EXAMPLE A4

Preparation of intermediate compound 4

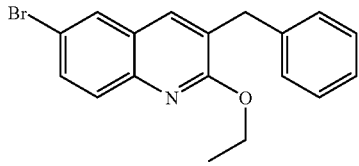

A mixture of intermediate compound 2 (prepared according to A2) (0.045 mol) in NaOEt 21% in ethanol (50 ml) and ethanol (150 ml) was stirred and refluxed for 12 hours. The mixture was poured out on ice and extracted with CH$_2$Cl$_2$. The organic layer was separated, dried (MgSO$_4$), filtered and the solvent was evaporated.

Yielding: 15.2 g of intermediate compound 4 (98%).

EXAMPLE A5

Preparation of intermediate compound 5

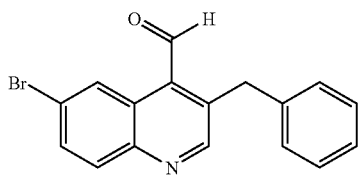

A mixture of 5-bromo-1H-indole-2,3-dione (0.28 mol) in NaOH 3N (650 ml) was stirred and heated at 80° C. for 30 min, then cooled to room temperature. Benzenepropanal (0.28 mol) was added and the mixture was stirred and refluxed overnight. The mixture was allowed to cool to room temperature and acidified till pH=5 with HOAc. The precipitate was filtered off, washed with H$_2$O and dried (vacuum). Yielding: 50 g of intermediate compound 5 (52%).

EXAMPLE A6

Preparation of intermediate compound 6

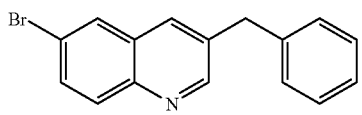

A mixture of intermediate compound 5 (prepared according to A5) (0.035 mol) in diphenylether (100 ml) was stirred and heated at 300° C. for 8 hours, then allowed to cool to room temperature. This procedure was carried out four times. The four mixtures were combined and then purified by column chromatography over silica gel (eluent: CH$_2$Cl$_2$/CH$_3$OH 100/0, then 99/1). The pure fractions were collected and the solvent was evaporated. Yielding: 25.6 g of intermediate compound 6 (61%).

EXAMPLE A7

Preparation of intermediate compound 7 and 8

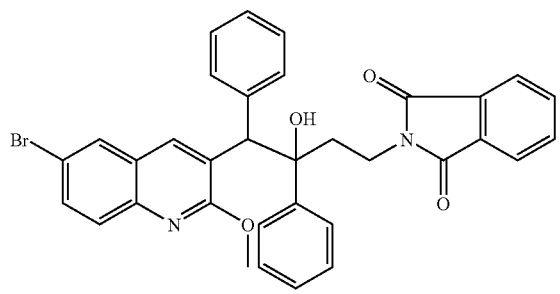

Intermediate 7 = (A)
Intermediate 8 = (B)

nBuLi 1.6M (0.13 mol) was added dropwise at −10° C. under N$_2$ flow to a mixture of N-(1-methylethyl)-2-propanamine (0.13 mol) in THF (300 ml). The mixture was stirred at −10° C. for 20 min and then cooled to −70° C. A solution of intermediate compound 3 (prepared according to A3) (0.1 mol) in THF (300 ml) was added dropwise. The mixture was stirred at −70° C. for 45 min. A solution of 2-(3-oxo-3-phenylpropyl)-1H-isoindole-1,3(2H)-dione (0.13 mol) in THF (300 ml) was added dropwise. The mixture was stirred at −70° C. for 1 hour, then brought to 40° C., stirred at 40° C. for 2 hours, hydrolyzed at 40° C. with H₂O and extracted with EtOAc. The organic layer was separated, dried (MgSO₄), filtered and the solvent was evaporated. The residue (40 g) was purified by column chromatography over silica gel (eluent: cyclohexane/EtOAc 85/15). Two pure fractions were collected and their solvents were evaporated. Yielding: 1.8 g of intermediate compound 7 (3%) and 5.3 g of intermediate compound 8 (9%).

EXAMPLE A8

Preparation of intermediate compounds 12 and 13

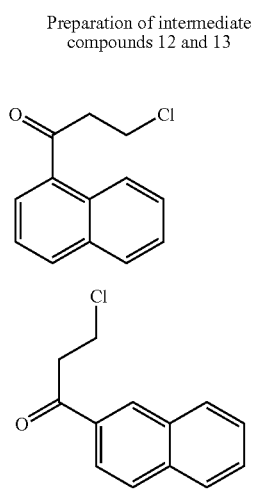

Intermediate 12

Intermediate 13

A mixture of aluminium chloride (34.3 g, 0.257 mol) and 3-chloropropionyl chloride (29.7 g, 0.234 mol) in dichloroethane (150 ml) was stirred at 0° C. A solution of naphtalene (30 g, 0.234 mol) in dichloroethane (50 ml) was added. The mixture was stirred at 5° C. for 2 hours and poured out into ice water. The organic layer was separated, dried (MgSO₄), filtered, and the solvent was evaporated. The residue (56 g) was purified by column chromatography over silica gel (eluent: cyclohexane/CH₂Cl₂: 60/40; 20-45 μm). Two fractions were collected and the solvent was evaporated to afford intermediate compound 12 (31 g; Yield=61%) as an oil. The second fraction (14 g) was taken up in DIPE to afford intermediate compound 13 (8.2 g; Yield=16%; mp. 68° C.) as a pale yellow solid.

EXAMPLE A9

Preparation of intermediate compound 14

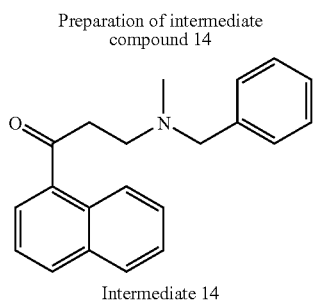

Intermediate 14

A mixture of the intermediate compound 12 (prepared according to A8) (3 g; 0.0137 mol), N-benzylmethyl amine (2 ml; 0.0150 mol) in acetonitrile (100 ml) was stirred at 80° C. for 2 hours. At room temperature (RT) water was added. The mixture was extracted with CH₂Cl₂. The organic layer was separated and dried (MgSO₄), filtered, and the solvent was evaporated. The residue (6 g) was purified by column chromatography over silica gel (eluent: CH₂Cl₂/MeOH: 97/3; 20-45 μm) to afford BB 1 (4.2 g; quantitative yield) as an oil, yielding intermediate compound 14.

EXAMPLE A10

Preparation of intermediate compound 15

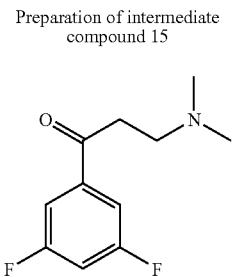

A mixture of 3,5-difluoroacetophenone (commercially available) (25 g; 0.16 mol), diethylamine hydrochloride (52 g; 0.64 mol), paraformaldehyde (19 g; 0.63 mol) in HCl conc (5 ml) and ethanol (300 ml) was stirred at 80° C. for 16 hours. The mixture was evaporated till dryness and the residue was taken up by HCl 3N (50 ml). This mixture was extracted with Et₂O (3×30 ml). The organic layer was collected and basified with K₂CO₃ (10% aq). The organic layer was dried over MgSO₄ and evaporated. The product, intermediate compound 15 was used without further purification for the next step (23.7 g; yield: 69%) as an oil.

B. Preparation of the Final Compounds

EXAMPLE B1

Preparation of final compound 1, 2, 3 and 4

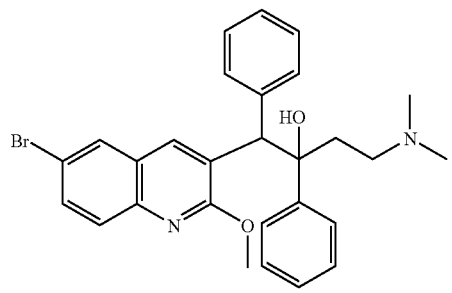

Compound 1 (A1)
Compound 2 (A2)
Compound 3 (A)
Compound 4 (B)

nBuLi 1.6M (0.067 mol) was added slowly at −20° C. under N₂ flow to a solution of N-(1-methylethyl)-2-propanamine (0.067 mol) in THF (100 ml). The mixture was cooled to −70° C. A solution of intermediate compound 3 (prepared according to A3) (0.122 mol) in THF (200 ml) was added slowly. The mixture was stirred at −70° C. for 30 min. A solution of 3-(dimethylamino)-1-phenyl-1-propanone (0.146 mol) in THF (100 ml) was added slowly. The mixture was stirred at −70° C. for 1 hour, then hydrolysed at −30° C. with ice water and extracted with EtOAc. The organic layer was separated, dried (MgSO$_4$), filtered and the solvent was evaporated. The residue (67 g) was purified by column chromatography over silica gel (eluent: CH$_2$Cl$_2$/CH$_3$OH/NH$_4$OH 99/1/0.1; 20-45 μm). Two pure fractions were collected and their solvents were evaporated. Fraction 1 (7.2 g) was crystallized from DIPE. The precipitate was filtered off and dried. Yielding: 6.5 g of diastereoisomer A (final compound 3) (mp. 172° C.) (10%) as a white solid. Fraction 2 (13 g) was crystallized from 2-propanone and diethyl ether. The precipitate was filtered off and dried.

Yielding: 11 g of diastereoisomer B (final compound 4) (mp. 170° C.) (17%) as a white solid. Part of fraction of final compound 3 (4 g) was separated into its enantiomers by column chromatography (eluent: hexane/2-propanol 99.9/0.1; column: CHIRACEL OD). Two pure fractions were collected and their solvents were evaporated The residue was crystallized from pentane. The precipitate was filtered off and dried.

Yielding: 0.7 g of enantiomer A1 (final compound 1) (mp. 194° C.) and 0.6 g of enantiomer A2 (final compound 2) (mp. 191° C.) as a white solid.

EXAMPLE B2

Preparation of final compound 5 and 6

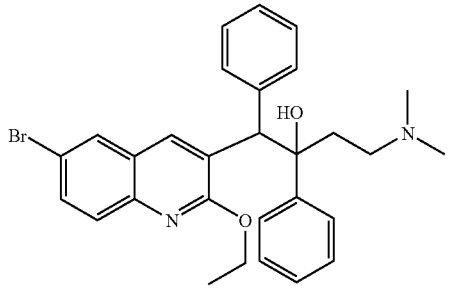

Compound 5 (A)
Compound 6 (B)

nBuLi 1.6M (0.048 mol) was added slowly at −20° C. to a solution of N-(1-methylethyl)-2-propanamine (0.048 mol) in THF (70 ml). The mixture was cooled again to −70° C. A solution of intermediate compound 4 (prepared according to A4) (0.044 mol) in THF (150 ml) was added slowly. The mixture was stirred at −70° C. for 30 min. A solution of 3-(dimethylamino)-1-phenyl-1-propanone (0.053 mol) in THF (100 ml) was added slowly. The mixture was stirred at −70° C. for 1 hour, hydrolysed at −30° C. with ice water and extracted with EtOAc. The organic layer was separated, dried (MgSO$_4$), filtered and the solvent was evaporated. The residue (23.5 g) was purified by column chromatography over silica gel (eluent: CH$_2$Cl$_2$/CH$_3$OH/NH$_4$OH 99.5/0.5/0.1; 15-40 μm). Two pure fractions were collected and their solvents were evaporated. The residue was crystallized from DIPE. The precipitate was filtered off and dried.

Yielding: 0.7 g of final compound 5 (3%) (mp. 162° C.) as a white solid and 1g of final compound 6 (5%) (mp. 74° C.) as a white solid.

EXAMPLE B3

Preparation of final compound 7 and 8

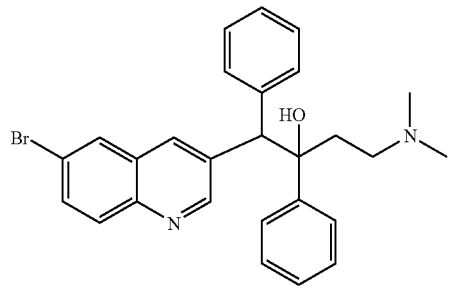

Compound 7 (A)
Compound 8 (B)

nBuLi (1.6M) (0.070 mol) was added dropwise at −30° C. under N$_2$ flow to a solution of N-(1-methylethyl)-2-propanamine (0.070 mol) in THF (70 ml). The mixture was stirred at −20° C. for 30 min, then cooled to −70° C. A solution of intermediate compound 6 (prepared according to A6) (0.046 mol) in THF (130 ml) was added dropwise. The mixture was stirred at −70° C. for 45 min. A solution of 3-(dimethylamino)-1-phenyl-1-propanone (0.056 mol) in THF (100 ml) was added dropwise. The mixture was stirred at −70° C. for 2 hours, hydrolyzed with ice-water and extracted with EtOAc. The organic layer was separated, dried (MgSO$_4$), filtered and the solvent was evaporated. The residue (23.6 g) was purified by column chromatography over silica gel (eluent: CH$_2$Cl$_2$/CH$_3$OH/NH$_4$OH 99/1/0.1; 15-40 μm). Two pure fractions were collected and their solvents were evaporated. Fraction 1 (4 g) was crystallized from diethyl ether. The precipitate was filtered off and dried. Yielding: 1.7 g of final compound 7 (mp. 98° C.) (7.6%). Fraction 2 (3.5 g) was crystallized from dietyl ether/EtOAc. The precipitate was filtered off and dried. Yielding: 2.2 g of final compound 8 (mp. 180° C.) (9.8%) as a white solid.

EXAMPLE B4

Preparation of final compound 9

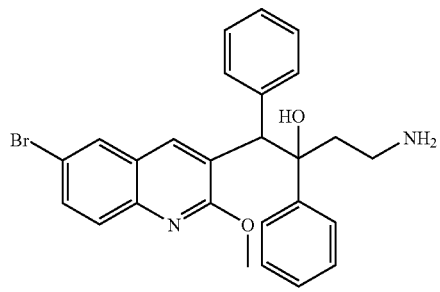

A mixture of intermediate compound 8 (prepared according to A7) (0.009 mol) and hydrazine (0.01 mol) in ethanol (70 ml) was stirred and refluxed for 1 hour. The solvent was evaporated till dryness. The residue was dissolved in CH₂Cl₂. The organic solution was washed with K₂CO₃ 10%, dried (MgSO₄), filtered and the solvent was evaporated. The residue (5 g) was purified by column chromatography over silica gel (eluent: CH₂Cl₂/CH₃OH/NH₄OH 97/3/0.1; 15-40 μm). The pure fractions were collected and the solvent was evaporated. The residue was crystallized from diethyl ether. The precipitate was filtered off and dried. Yielding: 2.6 g of final compound 9 (mp. 204° C.) (62%) as a pale yellow solid.

EXAMPLE B5

Preparation of final compound 10

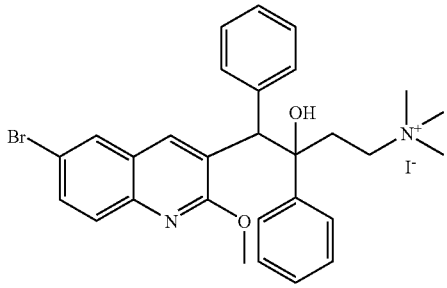

CH₃I (0.0033 mol) was added at room temperature to a solution of final compound 4 (prepared according to B1) (0.003 mol) in 2-propanone (15 ml). The precipitate was filtered off and dried. Yielding: 1.2 g of final compound 10 (mp. 198° C.) (62%) as a pale yellow solid.

EXAMPLE B6

Preparation of final compound 11

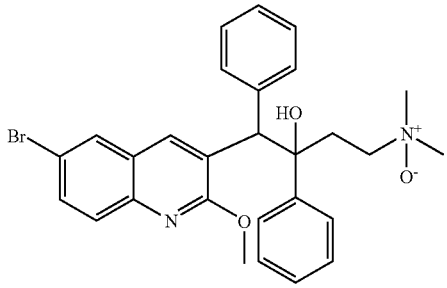

A solution of 3-chloroperoxybenzoic acid (0.0069 mol) in CH₂Cl₂ (35 ml) was added dropwise at room temperature to a solution of final compound 4 (prepared according to B1) (0.0069 mol) in CH₂Cl₂ (35 ml). The mixture was stirred at room temperature for 1 hour, washed with K₂CO₃ 10%, dried (MgSO₄), filtered and the solvent was evaporated. The residue was crystallized from diethyl ether. The precipitate was filtered off and dried. Yielding: 1.8 g of final compound 11 (mp. 208° C.) as a white solid.

EXAMPLE B7

Preparation of final compound 12, 13, 12a, 13a, 14 and 15

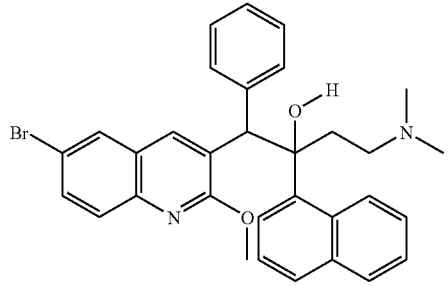

Compound 14 (A)
Compound 15 (B)

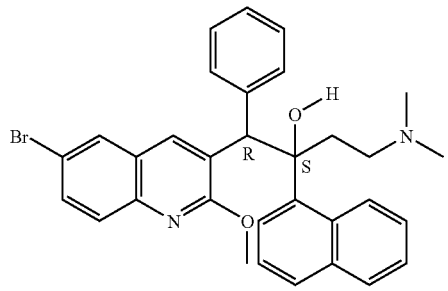

Compound 12 (A1)
[alpha]$_D^{20}$ = -166.98 (c = 0.505 g/100 ml in DMF)

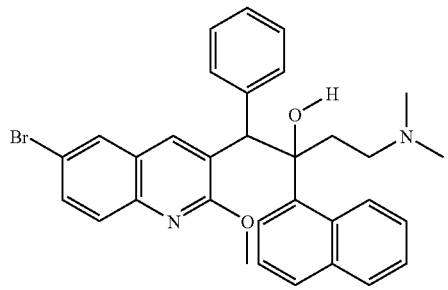

Compound 12a (B1)
[alpha]$_D^{20}$ = -42.56 (c = 0.336 g/100 ml in DMF)

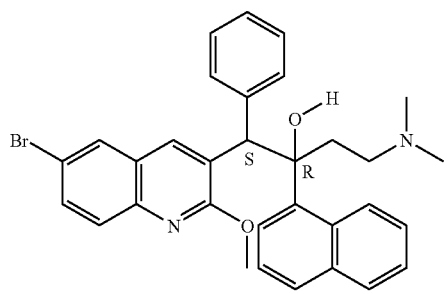

Compound 13 (A2)
[alpha]$_D^{20}$ = +167.60 (c = 0.472 g/100 ml in DMF)

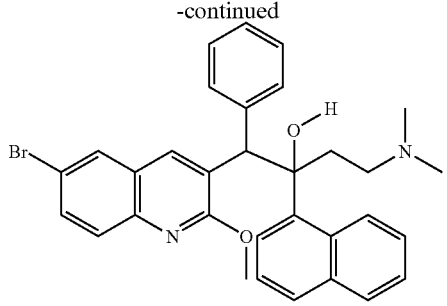

Compound 13a (B2)
[alpha]$_D^{20}$ = +43.55 (c = 0.349 g/100 ml in DMF)

nBuLi 1.6M (0.05 mol) was added slowly at −20° C. under N2 flow to a solution of N-(1-methylethyl)-2-propanamine (0.05 mol) in THF (80 ml). The mixture was stirred at −20° C. for 15 minutes, then cooled to −70° C. A solution of intermediate compound 3 (prepared according to A3) (0.046 mol) in THF (150 ml) was added slowly. The mixture was stirred at −70° C. for 30 minutes. A solution of 0.055 mol of 3-(dimethylamino)-1-(1-naphthyl)-1-propanone in THF (120 ml) was added slowly. The mixture was stirred at −70° C. for 3 hours, hydrolyzed at −30° C. with ice water and extracted with EtOAc. The organic layer was separated, dried (MgSO$_4$), filtered, and the solvent was evaporated. The residue (29 g) was purified by column chromatography over silica gel (eluent: CH$_2$Cl$_2$/CH$_3$OH/NH$_4$OH; 99.5/0.5/0.1; 15-35 μm). Two fractions were collected and the solvent was evaporated, yielding: 3 g fraction 1 and 4.4 g of fraction 2. Fraction 1 and 2 were crystallized separately from DIPE. The precipitate was filtered off and dried, yielding: 2.2 g of diastereoisomer A final compound 14 (Yield: 9%; mp. 210° C.) as a white solid and 4 g of diastereoisomer B final compound 15 (Yield: 16%; mp. 244° C.) as a white solid. To obtain the corresponding enantiomers, diastereoisomer A (final compound 14) was purified by chiral chromatography over silica gel (chiralpack AD) (eluent: hexane/EtOH; 99.95/0.05). Two fractions were collected and the solvent was evaporated. Yield: 0.233 g of enantiomer A1 (final compound 12) (mp. 118° C., [α]$_D^{20}$=166.98° (c=0.505 g/100 ml in DMF)) as a white solid and 0.287 g of enantiomer A2 (final compound 13) (mp. 120° C., [α]$_D^{20}$=+167.60° (c=0.472 g/100 ml in DMF)) as a white solid.

0.2 g of diastereoisomer B (final compound 15) was purified by chiral chromatography over silica gel (chiralpack AD) (eluent: EtOH/iPrOH/N-ethyl-ethanamine; 50/50/0.1). Two fractions were collected and the solvent was evaporated. Yield: 78.2 mg of enantiomer B 1 and 78.8 mg of enantiomer B2. Enantiomer B1 was purified by column chromatography over silica gel (eluent: CH$_2$Cl$_2$/CH$_3$OH/NH$_4$OH; 99/1/0.1; 15-40 μm). One fraction was collected and the solvent was evaporated. Yield: 57 mg of enantiomer B1 (final compound 12a) ([α]$_D^{20}$=−42.56° (c=0.336 g/100 ml in DMF)). Enantiomer B2 was purified by column chromatography over silica gel (eluent: CH$_2$Cl$_2$/CH$_3$OH/NH$_4$OH; 99/1/0.1; 15-40 μm). One fraction was collected and the solvent was evaporated. Yield: 53 mg of enantiomer B2 (final compound 13a) ([α]$_D^{20}$=+43.55° (c=0.349 g/100 ml in DMF)).

EXAMPLE B8

Preparation of final compounds 67, 68, 110 and 111

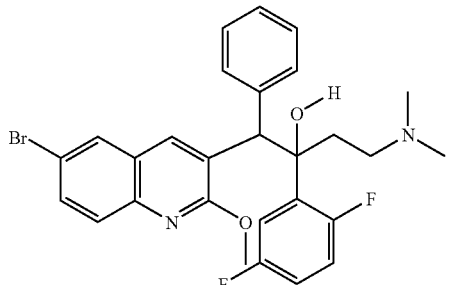

compound 67(A)
compound 68(B)
final compound 110 (A1)
final compound 111 (A2)

nBuLi 1.6M (0.067 mol) was added slowly at −20° C. under N$_2$ flow to a solution of N-(1-methylethyl)-2-propanamine (0.0104 mol) in THF (50 ml). The mixture was cooled to −70° C. A solution of intermediate compound 3 (prepared according to A3) (0.0087 mol) in THF (50 ml) was added slowly. The mixture was stirred at −70° C. for 30 min. A solution of 3-(dimethylamino)-1-(2,5-difluorophenyl)-1-propanone (0.0122 mol) in THF (20 ml) was added slowly. The mixture was stirred at −70° C. for 1 hour, then hydrolysed at −30° C. with ice water and extracted with EtOAc. The organic layer was separated, dried (MgSO$_4$), filtered off and the solvent was evaporated. The residue (6.3 g) was purified by column chromatography over silica gel (eluent: CH$_2$Cl$_2$/CH$_3$OH/NH$_4$OH 98/2/0.2; 20-45 μm). Two pure fractions were collected and their solvents were evaporated. Fraction 1 (1.2 g) was crystallized from Et$_2$O. The precipitate was filtered off and dried. Yield: 0.63 g of diastereoisomer A (final compound 67)(mp. 60° C.; Y=13%) as a white solid. Fraction 2 (1 g) was crystallized from diethylether. The precipitate was filtered off and dried. Yield: 0.64 g of diastereoisomer B (final compound 68) (mp. 208° C.; Y=14%). 0.63 g of diastereoisomer A were purified by chiracel AD (eluent: heptane/iPrOH 99.95/0.05). Two fractions were collected corresponding to A1 enantiomer (final compound 110, 0.13 g; mp 167° C.) as a white solid and the A2 enantiomer (final compound 111, 0.086 g) as an oil.

EXAMPLE B9

Preparation of final compound 38, 39, 108 and 109

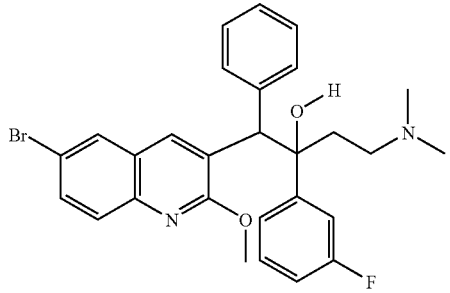

compound 38(A)
compound 39(B)
compound 108(A1)
compound 109(A2)

nBuLi 1.6M (0.04 mol) was added slowly at −20° C. under N₂ flow to a solution of N-(1-methylethyl)-2-propanamine (0.04 mol) in THF (50 ml). The mixture was cooled to −70° C. A solution of intermediate compound 3 (prepared according to A3) (0.037 mol) in THF (100 ml) was added slowly. The mixture was stirred at −70° C. for 30 min. A solution of 3-(dimethylamino-1-(3-fluorophenyl)-1-propanone (0.044 mol) in THF (50 ml) was added slowly. The mixture was stirred at −70° C. for 1 hour, then hydrolized at −30° C. with ice water and extracted with EtOAc. The organic layer was separated, dried (MgSO₄), filtered and the solvent was evaporated. The residue (20 g) was purified by column chromatography over silica gel (eluent: CH₂Cl₂/CH₃OH/NH₄OH 99.5/0.5/0.1; 15-40 μm). Three pure fractions were collected and their solvents were evaporated. Fraction 1 (2.8 g) was crystallized from DIPE. The precipitate was filtered off and dried. Yielding: 1.45 g (7%) of diastereoisomer A (final compound 38) (mp. 198° C.) as a white solid. Fraction 2 (3.4 g) was crystallized from DIPE. The precipitate was filtered off and dried. Yielding: 1.55 g (8%) of diastereoisomer B (final compound 39) (mp. 207° C.) as a white solid.

Part of fraction of final compound 38 (1 g) was separated into its enantiomers by chiral chromatography (eluent: hexane/2-propanol 99.9/0.1; column: CHIRACEL OD). Two pure fractions were collected and their solvents were evaporated. The residue was crystallized from pentane. The precipitate was filtered off and dried. Yield: 0.3 g of enantiomer A1 (final compound 108) (mp. 160° C.) as a white solid and 0.26 g of enantiomer A2 (final compound 109) (mp. 156° C.) as a white solid.

EXAMPLE B10

Preparation of final compound 71 and 72

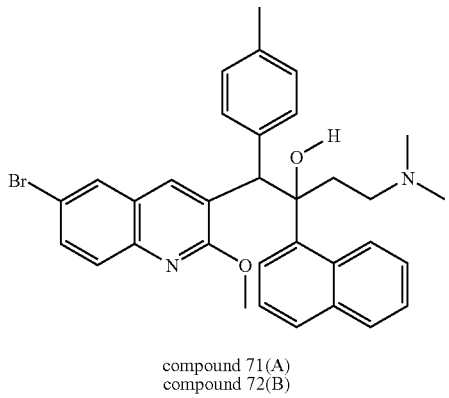

compound 71(A)
compound 72(B)

nBuLi 1.6M (0.0042 mol) was added slowly at −20° C. under N₂ flow to a solution of N-(1-methylethyl)-2-propanamine (0.0042 mol) in THF (20 ml). The mixture was cooled to −70° C. A solution of-intermediate compound 9 (prepared according to A1) (0.0038 mol) in THF (50 ml) was added slowly. The mixture was stirred at −70° C. for 30 min. A solution of 3-(dimethylamino)-1-(1-naphthyl)-1-propanone (0.0059 mol) in THF (20 ml) was added slowly. The mixture was stirred at −70° C. for 1 hour, then hydrolysed at −30° C. with ice water and extracted with EtOAc. The organic layer was separated, dried (MgSO₄), filtered and the solvent was evaporated. The residue (2.2 g) was purified by column chromatography over silica gel (eluent: CH₂Cl₂/CH₃OH/NH₄OH 99/1/0.1; 15-40 μm). Two pure fractions were collected and their solvents were evaporated. Fraction 1 (0.17 g) was crystallized from Et₂O. The precipitate was filtered off and dried. Yield: 0.05 g of diastereoisomer A (final compound 71)(mp. 174° C.; Yield=3%) as a white solid. Fraction 2 (0.27 g) was crystallized from diethyl ether. The precipitate was filtered off and dried. Yield: 0.053 g of diastereoisomer B (final compound 72) (mp. 178° C.; Yield=4%) as a white solid.

EXAMPLE B11

Preparation of final compound 99

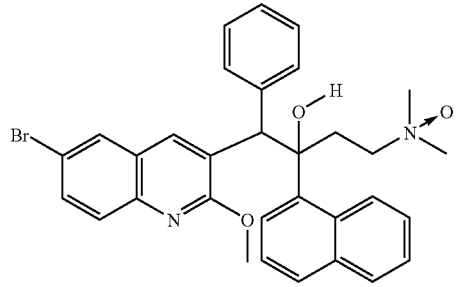

compound 99 (A1)

A solution of 3-chloroperoxybenzoic acid (0.0036 mol) in CH₂Cl₂ (10 ml) was added dropwise at room temperature to a solution of final compound 12 (enantiomer A1) (prepared according to B7) (0.0069 mol) in CH₂Cl₂ (35 ml). The mixture was stirred at room temperature for 1 hour, washed with K₂CO₃ 10%, dried (MgSO₄), filtered and the solvent was evaporated. The residue was crystallized from diethyl ether. The precipitate was filtered off and dried. Yielding: 0.16 g final compound 99 (mp. 218° C.; Y=78%) as a white solid.

EXAMPLE B12

Preparation of final compound 110

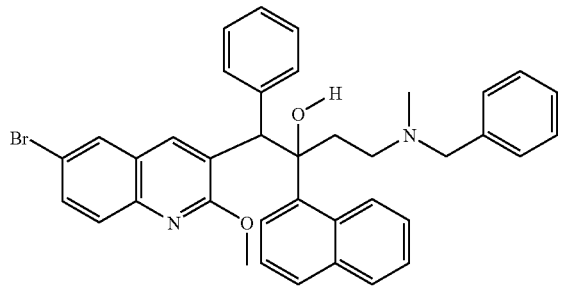

nBuLi 1.6M (0.0075 mol) was added slowly at −20° C. under N₂ flow to a solution of N-(1-methylethyl)-2-propanamine (0.0075 mol) in THF (30 ml). The mixture was cooled to −70° C. A solution of intermediate compound 3 (prepared according to A3) (0.0062 mol) in THF (20 ml) was added slowly. The mixture was stirred at −70° C. for 30 min. A solution of 0.0075 mol of intermediate compound 14 (prepared according to Example A9) in THF (10 ml) was added slowly. The mixture was stirred at −70° C. for 90 minutes, then hydrolysed at −30° C. with ice water and extracted with EtOAc. The organic layer was separated, dried (MgSO₄), filtered and the solvent was evaporated. The residue (3 g) was purified by column chromatography over silica gel (eluent:

Cyclohexane/EtOAc 90/10; 15-40 μm). The final compound 110 (1.5 g; Yield=38%) was obtained as an oil.

EXAMPLE B13

Preparation of final compound 111 and 112

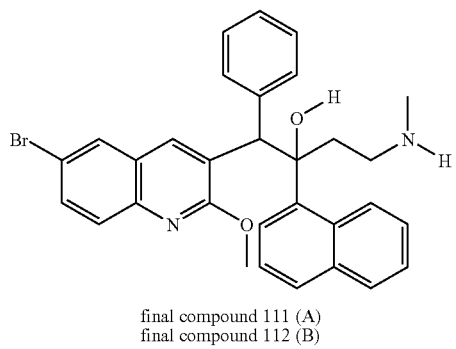

final compound 111 (A)
final compound 112 (B)

1-chloroethyl chloroformate (0.25 ml, 0.0023 mol) was added at room temperature under nitrogen to a solution of the derived III (1.5 gr, 0.0023 mol) in dichloromethane (30 ml). The mixture was stirred at 80° C. for 1 hour. The solvent was evaporated and the methanol (15 ml) was added. The mixture was stirred and refluxed for 30 minutes. After evaporation, the residue (1.49 gr) was purified by column chromatography over silica gel (15-40 μm). The first fraction collected was crystallized from DIPE to afford (0.168 gr; mp. 204° C.; Yield=13%) final compound 111 as the A diastereoisomer. The second fraction collected was corresponded to final compound 112 as the B diastereoisomer (0.298 g; mp. 225° C.; Yield=23%).

EXAMPLE B14

Preparation of final compounds 113 and 114

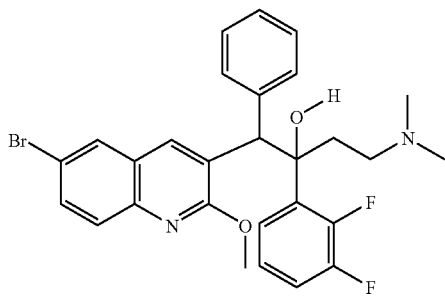

(A) final compound 113
(B) final compound 114 nBuLi 1.6M (3.5 ml; 0.0056 mol) was added slowly at –20° C. under N$_2$ flow to a solution of N-(1-methylethyl)-2-propanamine (770 μl; 0.0055 mol) in THF (20 ml). The mixture was cooled to –70° C. A solution of intermediate compound 3 (prepared according to A3) (1.5 g; 0.0047 mol) in THF (20 ml) was added slowly. The mixture was stirred at –70° C. for 30 min. A solution of intermediate compound 15 (1 g; 0.0047 mol) in THF (10 ml) was added slowly. The mixture was stirred at –70° C. for 3 hours, then hydrolysed at –30° C. with ice water and extracted with EtOAc. The organic layer was separated, dried (MgSO$_4$), filtered off and the solvent was evaporated. The residue (2.8 g) was purified by column chromatography over silica gel (eluent: CH$_2$Cl$_2$/CH$_3$OH/NH$_4$OH 99/1/0.1; 15-40 μm). Two pure fractions were collected and their solvents were evaporated. Fraction 1 (0.149 g) was crystallized from DIPE to afford final compound 113 (0.14 g; mp. 185° C.; Yield=6%) as a white powder.

Fraction 2 (0.14 g) was crystallized from Et$_2$O to afford final compound 114 (0.14 g; mp. 210° C.; Yield=6%) as a white powder.

EXAMPLE B15

Preparation of final compounds 115, 116, 117 and 118

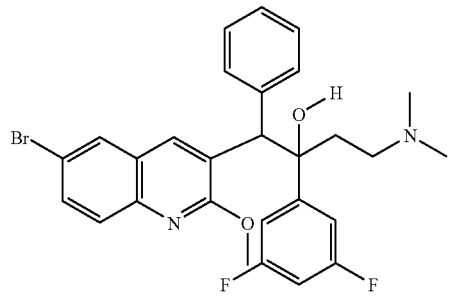

final compound 115 (A diastereoisomer)
final compound 116 (B diastereoisomer)
final compound 117 (A1 enantiomer)
final compound 118 (A2 enantiomer)

nBuLi 1.6M (4.6 ml; 0.6074 mol) was added slowly at –20° C. under N$_2$ flow to a solution of N-(1-methylethyl)-2-propanamine (1 ml; 0.0071 mol) in THF (20 ml). The mixture was cooled to –70° C. A solution of intermediate compound 15 (prepared according to A10) (2 g; 0.0061 mol) in THF (10 ml) was added slowly. The mixture was stirred at –70° C. for 30 min. A solution of 3-(dimethylamino)-1-(3,5-difluorophenyl)-1-propanone (prepared according to A10) (2 g; 0.0094 mol) in THF (15 ml) was added slowly. The mixture was stirred at –70° C. for 2 hours, then hydrolysed at –30° C. with NH$_4$Cl 10% aq and extracted with EtOAc. The organic layer was separated, dried (MgSO$_4$), filtered off and the solvent was evaporated. The residue (4.5 g) was purified by column chromatography over silica gel (eluent: CH$_2$Cl$_2$/iPrOH/NH$_4$OH 99.5/0.5/0.05; 15-40 μm). Two pure fractions were collected and their solvents were evaporated. Fraction 1 (0.67 g; Yield=20%) was crystallized from DIPE to afford final compound 115 (0.29 g; mp. 192° C.; Yield=9%) as a white powder. Fraction 2 (0.46 g) was crystallized from Et$_2$O to afford final compound 116 (0.22 g; mp. 224° C.; Yield=7%) as a white powder. From 0.1 g of final compound 115, final compounds 116 and 117 (enantiomers) were separated over CHIRACEL OD (eluent: Heptane/iPrOH 99.9/0.1; 15-40 μm). Two fractions were collected and crystallized from Et$_2$O to afford final compound 116 (0.05 g; mp. 161° C.; Yield=100%) as a white powder and final compound 117 (0.043 g; mp 158° C.; Yield=98%) as a white powder.

The following final compounds were prepared according to the methods described above:

TABLE 1

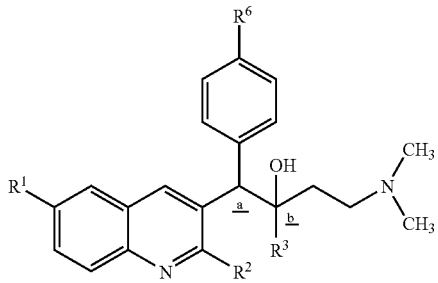

| Comp. nr. | Ex. nr. | R¹ | R² | R³ | R⁶ | Stereochemistry and melting points | absolute configuration of carbon atom a or b |
|---|---|---|---|---|---|---|---|
| 1 | B1 | Br | OCH₃ | phenyl | H | (A1); 194° C. | |
| 2 | B1 | Br | OCH₃ | phenyl | H | (A2); 191° C. | |
| 3 | B1 | Br | OCH₃ | phenyl | H | (A); 200° C. | |
| 4 | B1 | Br | OCH₃ | phenyl | H | (B); 190° C. | |
| 16 | B1 | Br | OCH₃ | 4-chlorophenyl | H | (A); 200° C. | |
| 17 | B1 | Br | OCH₃ | 4-chlorophenyl | H | (B); 190° C. | |
| 20 | B1 | Br | OCH₃ | 2-thienyl | H | (A); 96° C. | |
| 21 | B1 | Br | OCH₃ | 2-thienyl | H | (B); 176° C. | |
| 22 | B1 | CH₃ | OCH₃ | phenyl | H | (A); 148° C. | |
| 23 | B1 | CH₃ | OCH₃ | phenyl | H | (B); 165° C. | |
| 24 | B1 | Br | OCH₃ | 3-thienyl | H | (A); 162° C. | |
| 25 | B1 | Br | OCH₃ | 3-thienyl | H | (B); 160° C. | |
| 26 | B1 | phenyl | OCH₃ | phenyl | H | (A); 174° C. | |
| 27 | B1 | phenyl | OCH₃ | phenyl | H | (B); 192° C. | |
| 28 | B1 | F | OCH₃ | phenyl | H | (A); 190° C. | |
| 29 | B1 | F | OCH₃ | phenyl | H | (B); 166° C. | |
| 30 | B1 | Cl | OCH₃ | phenyl | H | (A); 170° C. | |
| 31 | B1 | Cl | OCH₃ | phenyl | H | (B); 181° C. | |
| 32 | B1 | Br | SCH₃ | phenyl | H | (A); 208° C. | |
| 33 | B1 | Br | SCH₃ | phenyl | H | (B); 196° C. | |
| 34 | B1 | OCH₃ | OCH₃ | phenyl | H | (A); 165° C. | |
| 35 | B1 | OCH₃ | OCH₃ | phenyl | H | (B); 165° C. | |
| 36 | B1 | Br | OCH₃ | phenyl | Cl | (A); 197° C. | |
| 37 | B1 | Br | OCH₃ | phenyl | Cl | (B); 221° C. | |
| 38 | B9 | Br | OCH₃ | 3-fluorophenyl | H | (A); 198° C. | |
| 39 | B9 | Br | OCH₃ | 3-fluorophenyl | H | (B); 207° C. | |
| 108 | B9 | Br | OCH₃ | 3-fluorophenyl | H | (A1); 160° C. | |
| 109 | B9 | Br | OCH₃ | 3-fluorophenyl | H | (A2); 156° C. | |
| 40 | B1 | H | OCH₃ | phenyl | H | (A); 152° C. | |
| 41 | B1 | H | OCH₃ | phenyl | H | (B); 160° C. | |
| 42 | B1 | H | OCH₃ | CH₃ | H | (A); 140° C. | |
| 43 | B1 | H | OCH₃ | CH₃ | H | (B); 120° C. | |
| 59 | B1 | Br | OH | phenyl | H | (A); >260° C. | |
| 60 | B1 | Br | OH | phenyl | H | (B); 215° C. | |
| 5 | B2 | Br | OCH₂CH₂ | phenyl | H | (A); 162° C. | |
| 6 | B2 | Br | OCH₂CH₂ | phenyl | H | (B); 74° C. | |
| 7 | B3 | Br | H | phenyl | H | (A); 98° C. | |
| 8 | B3 | Br | H | phenyl | H | (B); 180° C. | |
| 12 | B7 | Br | OCH₃ | 1-naphthyl | H | (A1); 118° C. | a = R; b = S |
| 13 | B7 | Br | OCH₃ | 1-naphthyl | H | (A2); 120° C. | a = S; b = R |
| 12a | B7 | Br | OCH₃ | 1-naphthyl | H | (B1); [α]_D^{20} = −42.56* | |
| 13a | B7 | Br | OCH₃ | 1-naphthyl | H | (B2); [α]_D^{20} = +43.55** | |
| 14 | B7 | Br | OCH₃ | 1-naphthyl | H | (A); 210° C. | |
| 15 | B7 | Br | OCH₃ | 1-naphthyl | H | (B); 244° C. | |
| 45 | B7 | Br | OCH₃ | 2-naphthyl | H | (A); 262° C. | |
| 46 | B7 | Br | OCH₃ | 2-naphthyl | H | (B); 162° C. | |
| 67 | B8 | Br | OCH₃ | 2,5-difluorophenyl | H | (A); 60° C. | |
| 68 | B8 | Br | OCH₃ | 2,5-difluorophenyl | H | (B); 208° C. | |
| 110 | B8 | Br | OCH₃ | 2,5-difluorophenyl | H | (A1); 167° C. | |
| 111 | B8 | Br | OCH₃ | 2,5-difluorophenyl | H | (A2); oil | |
| 69 | B1 | Br | OCH₃ | 2-fluorophenyl | H | (A); oil | |
| 70 | B1 | Br | OCH₃ | 2-fluorophenyl | H | (B); oil | |
| 71 | B1 | Br | OCH₃ | 1-naphthyl | CH₃ | (A); 174° C. | |
| 72 | B1 | Br | OCH₃ | 1-naphthyl | CH₃ | (B); 178° C. | |
| 73 | B1 | Br | OCH₃ | 1-naphthyl | Cl | (B); 174° C. | |
| 74 | B1 | Br | OCH₃ | 1-naphthyl | Cl | (A); 110° C. | |

TABLE 1-continued

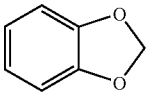

| Comp. nr. | Ex. nr. | $R^1$ | $R^2$ | $R^3$ | $R^6$ | Stereochemistry and melting points | absolute configuration of carbon atom a or b |
|---|---|---|---|---|---|---|---|
| 75 | B1 | Br | OCH$_3$ | 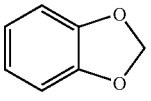 | H | (A); 196° C. | |
| 76 | B1 | Br | OCH$_3$ | 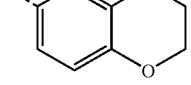 | H | (B); 130° C. | |
| 77 | B1 | Br | OCH$_3$ | 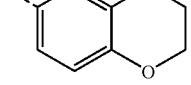 | H | (A); 202° C. | |
| 78 | B1 | Br | OCH$_3$ | 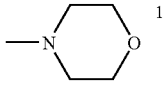 | H | (B); 202° C. | |
| 79 | B1 | Br | 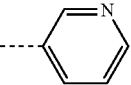 | 1-naphthyl | H | (A); >250° C. | |
| 80 | B1 | Br | OCH$_3$ | 4-cyanophenyl | H | (A); 224° C. | |
| 81 | B1 | Br | OCH$_3$ | 4-cyanophenyl | H | (B); 232° C. | |
| 82 | B1 | CH$_3$ | OCH$_3$ | 1-naphthyl | H | (A); 202° C. | |
| 83 | B1 | CH$_3$ | OCH$_3$ | 1-naphthyl | H | (B); 198° C. | |
| 84 | B1 | phenyl | OCH$_3$ | 1-naphthyl | H | (A); 248° C. | |
| 85 | B1 | phenyl | OCH$_3$ | 1-naphthyl | H | (B); 214° C. | |
| 86 | B1 | Br | OCH$_3$ | 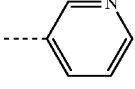 | H | (A); 184° C. | |
| 87 | B1 | Br | OCH$_3$ | 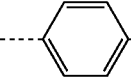 | H | (B); 186° C. | |
| 88 | B1 | Br | SCH$_3$ | 1-naphthyl | H | (A); 240° C. | |
| 89 | B1 | Br | OCH$_3$ | 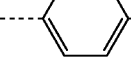 | H | (A); 236° C. | |
| 90 | B1 | Br | OCH$_3$ |  | H | (B); 206° C. | |
| 91 | B1 | H | OCH$_3$ | 1-naphthyl | H | (A); 178° C. | |
| 92 | B1 | H | OCH$_3$ | 1-naphthyl | H | (B); 160° C. | |

TABLE 1-continued

[Chemical structure: quinoline with R¹ substituent, R² at 2-position, attached at 3-position via carbon a to a 4-R⁶-phenyl group, and carbon b bearing OH, R³, and CH₂CH₂N(CH₃)₂]

| Comp. nr. | Ex. nr. | R¹ | R² | R³ | R⁶ | Stereochemistry and melting points | absolute configuration of carbon atom a or b |
|---|---|---|---|---|---|---|---|
| 93 | B1 | H | OCH₃ | 3-fluorophenyl | H | (A); 178° C. | |
| 94 | B1 | H | OCH₃ | 3-fluorophenyl | H | (B); 182° C. | |
| 95 | B1 | Br | OCH₃ | 2-phenylethyl | H | (A); 178° C. | |
| 96 | B1 | Br | OCH₃ | 2-phenylethyl | H | (B); 146° C. | |
| 97 | B1 | OCH₃ | OCH₃ | 1-naphthyl | H | (A); 168° C. | |
| 98 | B1 | OCH₃ | OCH₃ | 1-naphthyl | H | (B); 154° C. | |
| 113 | B14 | Br | OCH₃ | 2,3-difluorophenyl | H | (A); 128° C. | |
| 114 | B14 | Br | OCH₃ | 2,3-difluorophenyl | H | (B); 213° C. | |
| 115 | B15 | Br | OCH₃ | 3,5-difluorophenyl | H | (A); 192° C. | |
| 116 | B15 | Br | OCH₃ | 3,5-difluorophenyl | H | (B); 224° C. | |
| 117 | B15 | Br | OCH₃ | 3,5-difluorophenyl | H | (A1); 161° C. | |
| 118 | B15 | Br | OCH₃ | 3,5-difluoro-phenyl | H | (A2); 158° C. | |
| 119 | B7 | Cl | OCH₃ | 1-naphthyl | H | (A); 212° C. | |
| 120 | B7 | Cl | OCH₃ | 1-naphthyl | H | (B); 236° C. | |
| 122 | B7 | Br | OCH₃ | [acenaphthylenyl structure] | H | (B); 227° C. | |
| 127 | B7 | Br | OCH₃ | 5-bromo-2-naphthyl | H | (A); 226° C. | |
| 130 | B7 | Br | OCH₃ | 5-bromo-2-naphthyl | H | (B); 220° C. | |
| 131 | B1 | Br | OCH₃ | [tetrahydronaphthyl structure] | H | (A); 206° C. | |
| 134 | B9 | OCH₃ | OCH₃ | 3-fluorophenyl | H | (A); 172° C. | |
| 135 | B9 | OCH₃ | OCH₃ | 3-fluorophenyl | H | (B); 182° C. | |
| 143 | B7 | Br | OCH₃ | 3-bromo-1-naphthyl | H | (A); 234° C. | |
| 150 | B7 | Br | OCH₃ | 3-bromo-1-naphthyl | H | (B); 212° C. | |
| 159 | B8 | Br | OCH₃ | 2,5-difluorophenyl | H | (A1); 208° C. | |
| 160 | B8 | Br | OCH₃ | 2,5-difluorophenyl | H | (A2); 167° C. | |
| 162 | B7 | Br | OCH₃ | 6-methoxy-2-naphthyl | H | (A); 206° C. | |
| 163 | B7 | Br | OCH₃ | 6-methoxy-2-naphthyl | H | (B); 206° C. | |
| 164 | B9 | Br | [CH₂OCH₂CH₂OCH₃ group] | 3-fluorophenyl | H | (A); 118° C. | |

TABLE 1-continued

| Comp. nr. | Ex. nr. | R¹ | R² | R³ | R⁶ | Stereochemistry and melting points | absolute configuration of carbon atom a or b |
|---|---|---|---|---|---|---|---|
| 165 | B9 | Br | 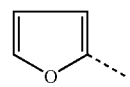 | 3-fluorophenyl | H | (B); oil | |
| 167 | B8 | Br | OCH₃ | 2,6-difluorophenyl | H | (B); 180° C. | |
| 174 | B9 | 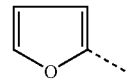 | OCH₃ | 3-fluorophenyl | H | (A); 159° C. | |
| 175 | B9 |  | OCH₃ | 3-fluorophenyl | H | (B); 196° C. | |
| 176 | B7 | Br | 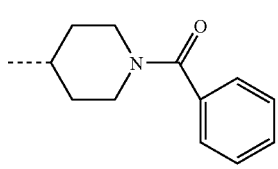 | 1-naphthyl | H | (A); oil | |
| 179 | B9 | CN | OCH₃ | 3-fluorophenyl | H | (A); 213° C. | |
| 180 | B9 | CN | OCH₃ | 3-fluorophenyl | H | (B); 163° C. | |
| 181 | B9 | Br | OCH₃ | 4-fluorophenyl | H | (A); 198° C. | |
| 182 | B9 | Br | OCH₃ | 4-fluorophenyl | H | (B); 238° C. | |
| 183 | B1 | Br | OCH₃ | 3-trifluoro-methylphenyl | H | (A); 170° C. | |
| 188 | B1 | Br | OCH₃ | 1,4-pyrimidin-2-yl | H | (A); 110° C. | |
| 189 | B1 | Br | OCH₃ | 1,4-pyrimidin-2-yl | H | (B); 145° C. | |
| 195 | B15 | Br | OCH₃ | 3,4-difluorophenyl | H | (A); 250° C. | |
| 196 | B15 | Br | OCH₃ | 3,4-difluorophenyl | H | (B); 184° C. | |
| 201 | B1 | Br | OCH₃ | 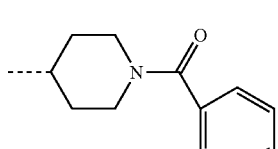 | H | (A): 214° C. | |
| 202 | B1 | Br | OCH₃ | 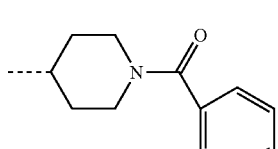 | H | (B); 246° C. | |

TABLE 1-continued

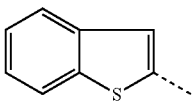

| Comp. nr. | Ex. nr. | R¹ | R² | R³ | R⁶ | Stereochemistry and melting points | absolute configuration of carbon atom a or b |
|---|---|---|---|---|---|---|---|
| 203 | B9 | benzothiophen-2-yl | OCH$_3$ | 3-fluorophenyl | H | (A); 225° C. | |
| 204 | B9 | benzothiophen-2-yl | OCH$_3$ | 3-fluorophenyl | H | (B); 216° C. | |
| 205 | B7 | Br | OCH$_3$ | 1-naphthyl | F | (A); 213° C. | |
| 206 | B7 | Br | OCH$_3$ | 1-naphthyl | F | (B); 213° C. | |
| 207 | B15 | F | OCH$_3$ | 3,5-difluorophenyl | H | (A); 232° C. | |
| 208 | B15 | F | OCH$_3$ | 3,5-difluorophenyl | H | (B); 188° C. | |
| 212 | B7 | (5-methylfuran-2-yl)methoxy | OCH$_3$ | 1-naphthyl | H | (B); 220° C. | |

*c = 0.336 g/100 ml in DMF
**c = 0.349 g/100 ml in DMF

TABLE 2

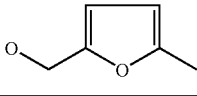

| Comp. nr. | Ex. nr. | R¹ | R² | R³ | R⁴ | R⁵ | Phys. data (salt/melting points) and stereochemistry |
|---|---|---|---|---|---|---|---|
| 18 | B1 | Br | OCH$_3$ | phenyl | CH$_2$CH$_3$ | CH$_2$CH$_3$ | ethanedioate (2:3); (A); 230°. |
| 19 | B1 | Br | OCH$_3$ | phenyl | CH$_2$CH$_3$ | CH$_2$CH$_3$ | ethanedioate (2:3), (B); 150° C. |
| 44 | B4 | Br | OCH$_3$ | phenyl | H | H | (A); 190° C. |
| 9 | B4 | Br | OCH$_3$ | phenyl | H | H | (B); 204° C. |
| 141 | B7 | Br | OCH$_3$ | 2-naphthyl | CH$_3$ | CH$_2$CH$_3$ | (A); 188° C. |
| 142 | B7 | Br | OCH$_3$ | 2-naphthyl | CH$_3$ | CH$_2$CH$_3$ | (B); 202° C. |
| 230 | B12 | Br | OCH$_3$ | 1-naphthyl | CH$_3$ | benzyl | /oil |
| 147 | B7 | Br | OCH$_3$ | 1-naphthyl | CH$_3$ | CH$_2$CH$_3$ | (A); 168° C. |
| 148 | B7 | Br | OCH$_3$ | 1-naphthyl | CH$_3$ | CH$_2$CH$_3$ | (B); 212° C. |

TABLE 2-continued

| Comp. nr. | Ex. nr. | R¹ | R² | R³ | R⁴ | R⁵ | Phys. data (salt/melting points) and stereochemistry |
|---|---|---|---|---|---|---|---|
| 56 | B13 | Br | OCH₃ | 1-naphthyl | CH₃ | H | (A); 204° C. |
| 214 | B13 | Br | OCH₃ | 1-naphthyl | CH₃ | H | (B); 225° C. |

TABLE 3

| Comp. nr. | Ex. nr. | R³ | L | Stereochemistry and melting points |
|---|---|---|---|---|
| 47 | 1 | phenyl | 1-piperidinyl | (A); 190° C. |
| 48 | B1 | phenyl | 1-piperidinyl | (B); 210° C. |
| 128 | B1 | 2-naphthyl | 1-piperidinyl | (A); 254° C. |
| 129 | B1 | 2-naphthyl | 1-piperidinyl | (B); 212° C. |
| 49 | B1 | phenyl | 1-imidazolyl | (A); 216° C. |
| 50 | B1 | phenyl | 1-imidazolyl | (B); 230° C. |
| 51 | B1 | phenyl | 1-(4-methyl)piperazinyl | (A); 150° C. |
| 52 | B1 | phenyl | 1-(4-methyl)piperazinyl | (B); 230° C. |
| 53 | B1 | phenyl | 1-(1,2,4-triazolyl) | (A); 180° C. |
| 54 | B1 | phenyl | 1-(1,2,4-triazolyl) | (B); 142° C. |
| 55 | B1 | phenyl | thiomorpholinyl | (A); oil |
| 57 | B5 | phenyl | –⁺N(CH₃)₃ I⁻ | (A); 244° C. |
| 10 | B5 | phenyl | –⁺N(CH₃)₃ I⁻ | (B); 198° C. |
| 58 | B6 | phenyl | –⁺N(CH₃)₂O⁻ | (A); 208° C. |
| 11 | B6 | phenyl | –⁺N(CH₃)₂O⁻ | (B); 208° C. |

TABLE 3-continued

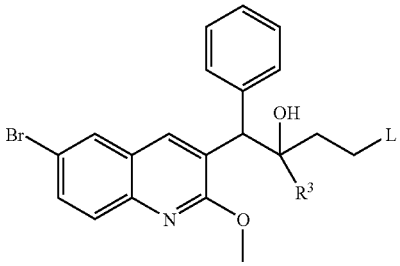

| Comp. nr. | Ex. nr. | R³ | L | Stereochemistry and melting points |
|---|---|---|---|---|
| 99 | B11 | 1-naphthyl | 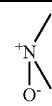 | (A1); 218° C. |
| 100 | B6 | 1-naphthyl |  | (A2); 218° C. |
| 101 | B6 | 1-naphthyl |  | (B); 175° C. |
| 102 | B5 | 1-naphthyl | 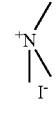 | (A2); 210° C. |
| 103 | B5 | 1-naphthyl |  | (B); >250° C. |
| 121 | B5 | 1-naphthyl |  | (A1); 210° C. |
| 123 | B1 | phenyl | morpholinyl | (A); 226° C. |
| 124 | B1 | phenyl | morpholinyl | (B); 210° C. |
| 136 | B7 | 2-naphthyl | 4-methylpyrazinyl | (A); 188° C. |
| 137 | B7 | 2-naphthyl | 4-methylpiperazinyl | (B); 232° C. |
| 139 | B7 | 2-naphthyl | morpholinyl | (A); 258° C. |
| 140 | B7 | 2-naphthyl | morpholinyl | (B); 214° C. |
| 144 | B7 | 2-naphthyl | pyrrolidinyl | (A); 238° C. |
| 145 | B7 | 1-naphthyl | 1-piperidinyl | (A); 212° C. |
| 146 | B7 | 1-naphthyl | 1-piperidinyl | (B); 220° C. |
| 149 | B7 | 1-naphthyl | 4-methylpyrazinyl | (B); 232° C. |
| 151 | B7 | 3-bromo-1-naphthyl | 4-methylpiperazinyl | (A); 178° C. |
| 152 | B7 | 3-bromo-1-naphthyl | 4-methylpiperazinyl | (B); 226° C. |
| 153 | B7 | 6-bromo-2-naphthyl | 4-methylpiperazinyl | (A); 208° C. |
| 154 | B7 | 6-bromo-2-naphthyl | 4-methylpiperazinyl | (B); 254° C. |
| 155 | B7 | 6-bromo-2-naphthyl | 1-piperidinyl | (A); 224° C. |
| 156 | B7 | 1-naphthyl | 4-methylpiperazinyl | (A); 200° C. |
| 157 | B7 | 6-bromo-2-naphthyl | 1-pyrrolidinyl | (B); 220° C. |
| 158 | B7 | 1-naphthyl | morpholinyl | (B); 272° C. |
| 166 | B7 | 6-bromo-2-naphthyl | 1-piperidinyl | (B); 218° C. |
| 170 | B7 | 2-naphthyl | 1-pyrrolidinyl | (A); 238° C. |
| 171 | B7 | 2-naphthyl | 1-pyrrolidinyl | (B); 218° C. |
| 172 | B7 | 1-naphthyl | 1,2,4-triazol-1-yl | /142° C. |
| 173 | B7 | 1-naphthyl | 1,2-imidazol-1-yl | (A); 222° C. |
| 177 | B7 | 6-bromo-2-naphthyl | morpholinyl | (A); 242° C. |
| 178 | B7 | 6-bromo-2-naphthyl | morpholinyl | (B); 246° C. |
| 187 | B7 | 1-naphthyl | 1,2-imidazol-1-yl | (B); 236° C. |

TABLE 3-continued

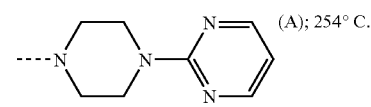

| Comp. nr. | Ex. nr. | R³ | L | Stereochemistry and melting points |
|---|---|---|---|---|
| 200 | B7 | 2-naphthyl | piperazinyl-pyrimidine | (A); 254° C. |
| 209 | B7 | 2-naphthyl | piperazinyl-pyrimidine | (B); 198° C. |

TABLE 4

| Comp. nr. | Ex. nr. | R³ | Q | L | Stereochemistry and melting points |
|---|---|---|---|---|---|
| 61 | B1 | phenyl | 0 | $N(CH_3)_2$ | (A); 220° C. |
| 62 | B1 | phenyl | 0 | $N(CH_3)_2$ | (B); 194° C. |
| 63 | B1 | phenyl | 2 | $N(CH_3)_2$ | (A); 150° C. |
| 64 | B1 | phenyl | 2 | $N(CH_3)_2$ | (B); 220° C. |
| 125 | B7 | 2-naphthyl | 2 | $N(CH_3)_2$ | (A); 229° C. |
| 126 | B7 | 2-naphthyl | 2 | $N(CH_3)_2$ | (B); 214° C. |
| 65 | B1 | phenyl | 3 | $N(CH_3)_2$ | (A); 130° C. |
| 66 | B1 | phenyl | 3 | $N(CH_3)_2$ | (B); 170° C. |
| 132 | B7 | 2-naphthyl | 2 | pyrrolidinyl | (A); 227° C. |
| 133 | B7 | 2-naphthyl | 2 | pyrrolidinyl | (B); 222° C. |
| 161 | B7 | 2-naphthyl | 2 | morpholinyl | (B); 234° C. |
| 186 | B7 | 1-naphthyl | 2 | $N(CH_3)_2$ | (A); 187° C. |
| 190 | B7 | 2-naphthyl | 3 | $N(CH_3)_2$ | (A); 170° C. |
| 191 | B7 | 2-naphthyl | 3 | $N(CH_3)_2$ | (B); 145° C. |
| 192 | B7 | 2-naphthyl | 2 | $N(CH_2CH_3)_2$ | (A); 90° C. |
| 193 | B7 | 2-naphthyl | 2 | $N(CH_2CH_3)_2$ | (B); 202° C. |
| 194 | B7 | 1-naphthyl | 2 | pyrrolidinyl | (B); 206° C. |
| 197 | B7 | 1-naphthyl | 3 | $N(CH_3)_2$ | (A); 160° C. |
| 198 | B7 | 2-naphthyl | 2 | morpholinyl | (A); 215° C. |
| 199 | B7 | 1-naphthyl | 2 | $N(CH_2)_3)_2$ | (A); 185° C. |
| 210 | B7 | 1-naphthyl | 2 | morpholinyl | (B); 222° C. |
| 211 | B7 | 1-naphthyl | 2 | morphoilinyl | (A); 184° C. |

TABLE 5

| Comp. nr. | Ex. nr. | $R^3$ | $R^8$ | $R^9$ | Stereochemistry and melting points |
|---|---|---|---|---|---|
| 104 | B1 | phenyl | —CH=CH—N= | | (A); 170° C. |
| 105 | B1 | phenyl | —CH=CH—N= | | (B); 150° C. |
| 106 | B1 | phenyl | $CH_3$ | =O | (A); 224° C. |
| 107 | B1 | phenyl | $CH_3$ | =O | (B); 180° C. |
| 138 | B7 | 1-naphthyl | H | =O | (A1); >260° C. |

TABLE 6

| Comp. nr. | Ex. nr. | $R^1$ a | $R^1$ b | $R^1$ c | $R^1$ d | $R^3$ | $R^6$ | Stereochemistry and melting points |
|---|---|---|---|---|---|---|---|---|
| 215 | B9 | H | Br | $CH_3$ | H | 3-fluorophenyl | H | (A); 197° C. |
| 216 | B9 | H | Br | $CH_3$ | H | 3-fluorophenyl | H | (B); 158° C. |
| 217 | B7 | H | H | Br | H | 1-naphthyl | H | (A); 212° C. |
| 218 | B7 | H | H | Br | H | 1-naphthyl | H | (B); 172° C. |
| 219 | B9 | H | Br | H | $CH_3$ | 3-fluorophenyl | H | (A); 220° C. |
| 220 | B9 | H | Br | H | $CH_3$ | 3-fluorophenyl | H | (B); 179° C |
| 221 | B7 | Br | H | H | H | 1-naphgthyl | H | (A); 170° C. |
| 224 | B7 | Br | H | H | H | 1-naphthyl | H | /205° C. |
| 222 | B7 | H | Br | H | H | 1-naphthyl | 3,4 (ring) | (A); 155° C. |
| 223 | B7 | H | Br | H | H | 1-naphthyl | 3,4 (ring) | (B); 205° C. |
| 225 | B7 | H | Br | $CH_3$ | H | 1-naphthyl | H | (A); 238° C. |
| 226 | B7 | H | Br | $CH_3$ | H | 1-naphthyl | H | (B); 208° C. |
| 227 | B15 | H | Br | $CH_3$ | H | 3,5-difluorophenyl | H | (A); 195° C. |
| 228 | B15 | H | Br | $CH_3$ | H | 3,5-difluorophenyl | H | (B); 218° C. |
| 229 | B7 | H | $CH_3$ | $CH_3$ | H | 1-naphthyl | H | (A); 238° C. |

C. PHARMACOLOGICAL EXAMPLES

C.1. In-vitro Method for Testing Compounds Against *M. Tuberculosis*.

Flat-bottom, sterile 96-well plastic microtiter plates were filled with 100 µl of Middlebrook (1×) broth medium. Subsequently, stock solutions (10×final test concentration) of compounds were added in 25 µl volumes to a series of duplicate wells in column 2 so as to allow evaluation of their effects on bacterial growth. Serial five-fold dilutions were made directly in the microtiter plates from column 2 to 11 using a customised robot system (Zymark Corp., Hopkinton, Mass.). Pipette tips were changed after every 3 dilutions to minimize pipetting errors with high hydrophobic compounds. Untreated control samples with (column 1) and without (column 12) inoculum were included in each microtiter plate. Approximately 5000 CFU per well of *Mycobacterium tuberculosis* (strain H37RV), in a volume of 100 µl in Middlebrook (1×) broth medium, was added to the rows A to H, except column 12. The same volume of broth medium without inoculum was added to column 12 in row A to H. The cultures were incubated at 37° C. for 7 days in a humidified atmosphere (incubator with open air valve and continuous ventilation). One day before the end of incubation, 6 days after inoculation, Resazurin (1:5) was added to all wells in a volume of 20 µl and plates were incubated for another 24 hours at 37° C. On day 7 the bacterial growth was quantitated fluorometrically.

The fluorescence was read in a computer-controlled fluorometer (Spectramax Gemini EM, Molecular Devices) at an excitation wavelength of 530 nm and an emission wavelength of 590 nm. The percentage growth inhibition achieved by the compounds was calculated according to standard methods, and MIC data (representing IC90's expressed in microgram/ml) were calculated. The results are shown in Table 5.

C.2. In-vitro Method for Testing Compounds for Anti-bacterial Activity Against Strain *M. Smegmatis* ATCC607.

Flat-bottom, sterile 96-well plastic microtiter plates were filled with 180 µl of sterile deionized water, supplemented with 0.25% BSA. Subsequently, stock solutions (7.8×final test concentration) of compounds were added in 45 µl volumes to a series of duplicate wells in column 2 so as to allow evaluation of their effects on bacterial growth. Serial five-fold dilutions (45 µl in 180 µl) were made directly in the microtiter plates from column 2 to 11 using a customised robot system (Zymark Corp., Hopkinton, Mass.). Pipette tips were changed after every 3 dilutions to minimize pipetting errors with high hydrophobic compounds. Untreated control samples with (column 1) and without (column 12) inoculum were included in each microtiter plate. Approximately 250 CFU per well of bacteria inoculum, in a volume of 100 µl in 2.8×Mueller-Hinton broth medium, was added to the rows A to H, except column 12. The same volume of broth medium without inoculum was added to column 12 in row A to H. The cultures were incubated at 37° C. for 48 hours in a humidified 5% $CO_2$ atmosphere (incubator with open air valve and continuous ventilation). At the end of incubation, two days after inoculation, the bacterial growth was quantitated fluorometrically. Therefore Alamar Blue (10×) was added to all wells in a volume of 20 µl and plates were incubated for another 2 hours at 50° C.

The fluorescence was read in a computer-controlled fluorometer (Cytofluor, Biosearch) at an excitation wavelength of 530 nm and an emission wavelength of 590 nm (gain 30). The % growth inhibition achieved by the compounds was calculated according to standard methods. The $pIC_{50}$ was defined as $-logIC_{50}$ wherein $IC_{50}$ is the 50% inhibitory concentration (M) for bacterial growth. The results are shown in Table 5.

TABLE 5

Results of an in vitro-screening of the compounds according to the invention for *M. tuberculosis* (MIC) and *M. smegmatis* ($pIC_{50}$).

| Co. No. | MIC | $pIC_{50}$ |
|---|---|---|
| 118 | 0.01 | 9.1 |
| 174 | 0.06 | 6.8 |
| 12 | 0.07 | 8.7 |
| 115 | 0.07 | 8.6 |
| 69 | 0.13 | 8.5 |
| 71 | 0.14 | 8.5 |
| 113 | 0.27 | 8.6 |
| 5 | 0.33 | 7.8 |
| 32 | 0.33 | 7.4 |
| 109 | 0.33 | 8.2 |
| 16 | 0.34 | 6.8 |
| 37 | 0.34 | 7.9 |
| 67 | 0.34 | 8.6 |
| 110 | 0.34 | 8.5 |
| 164 | 0.36 | 7.9 |
| 183 | 0.36 | 8.3 |
| 208 | 0.38 | 7.9 |

TABLE 5-continued

Results of an in vitro-screening of the compounds according to the invention for *M. tuberculosis* (MIC) and *M. smegmatis* ($pIC_{50}$).

| Co. No. | MIC | $pIC_{50}$ |
|---|---|---|
| 98 | 0.51 | 7.9 |
| 216 | 0.85 | 8.0 |
| 26 | 1.00 | 7.2 |
| 22 | 1.11 | 7.2 |
| 203 | 1.15 | 8.0 |
| 28 | 1.41 | 7.3 |
| 30 | 1.46 | 7.8 |
| 179 | 1.48 | 7.0 |
| 135 | 1.50 | 7.4 |
| 91 | 1.51 | 7.5 |
| 188 | 1.60 | 7.2 |
| 24 | 1.62 | 7.2 |
| 63 | 1.64 | 6.7 |
| 65 | 1.69 | 5.7 |
| 66 | 1.69 | 4.7 |
| 17 | 1.71 | 6.5 |
| 111 | 1.71 | 6.4 |
| 117 | 1.71 | 6.7 |
| 196 | 1.71 | 6.6 |
| 75 | 1.74 | 7.9 |
| 76 | 1.74 | 5.9 |
| 45 | 1.76 | 8.0 |
| 46 | 1.76 | 6.4 |
| 227 | 1.76 | 7.5 |
| 94 | 1.77 | 7.9 |
| 225 | 1.80 | 6.6 |
| 35 | 1.82 | 6.8 |
| 190 | 1.85 | 6.5 |
| 191 | 1.85 | 6.5 |
| 80 | 2.11 | 7.1 |
| 102 | 2.21 | 6.5 |
| 121 | 2.21 | 5.9 |
| 165 | 2.26 | 6.6 |
| 79 | 2.43 | 7.2 |
| 15 | 2.78 | 6.5 |
| 72 | 3.59 | 6.9 |
| 180 | 3.73 | 6.6 |
| 82 | 3.90 | 7.1 |
| 205 | 4.56 | 7.2 |
| 36 | 5.40 | 6.4 |
| 103 | 5.54 | 5.9 |
| 192 | 5.98 | 6.5 |
| 44 | 6.01 | 5.9 |
| 64 | 6.54 | 5.8 |
| 19 | 6.72 | 6.5 |
| 195 | 6.82 | 6.5 |
| 52 | 7.06 | 6.4 |
| 172 | 7.30 | 5.7 |
| 31 | 7.31 | 5.8 |
| 134 | 7.52 | 6.5 |
| 92 | 7.55 | 6.5 |
| 83 | 7.78 | 5.8 |
| 62 | 7.79 | 5.9 |
| 27 | 7.97 | 5.9 |
| 6 | 8.23 | 5.8 |
| 33 | 8.27 | 6.0 |
| 38 | 8.30 | 7.9 |
| 39 | 8.30 | 6.1 |
| 181 | 8.30 | 6.9 |
| 182 | 8.30 | 6.3 |
| 41 | 8.51 | 5.9 |
| 215 | 8.52 | 6.2 |
| 220 | 8.52 | 5.3 |
| 116 | 8.58 | 6.6 |
| 138 | 8.58 | 6.6 |
| 47 | 8.65 | 6.5 |
| 48 | 8.65 | 5.8 |
| 84 | 8.76 | 7.0 |
| 85 | 8.76 | 5.9 |
| 23 | 8.79 | 6.4 |
| 14 | 8.80 | 6.8 |
| 218 | 8.80 | 6.6 |
| 228 | 8.80 | 5.1 |
| 77 | 8.93 | 7.2 |

TABLE 5-continued

Results of an in vitro-screening of the compounds according to the invention for *M. tuberculosis* (MIC) and *M. smegmatis* (pIC$_{50}$).

| Co. No. | MIC | pIC$_{50}$ |
|---|---|---|
| 141 | 9.03 | 7.3 |
| 142 | 9.03 | 6.2 |
| 226 | 9.03 | 5.5 |
| 99 | 9.06 | 7.9 |
| 101 | 9.06 | 5.8 |
| 212 | 9.08 | 6.0 |
| 206 | 9.09 | 6.5 |
| 204 | 9.14 | 5.4 |
| 197 | 9.25 | 6.6 |
| 162 | 9.28 | 7.0 |
| 193 | 9.47 | 5.6 |
| 176 | 9.50 | 6.8 |
| 156 | 9.68 | 5.3 |
| 201 | 9.77 | 5.7 |
| 175 | 10.19 | 6.5 |
| 119 | 10.20 | 7.8 |
| 10 | 10.26 | 5.6 |
| 18 | 10.60 | 6.7 |
| 152 | 10.93 | 5.8 |
| 147 | 11.36 | 7.4 |
| 151 | 13.76 | 5.0 |
| 86 | 16.02 | 6.9 |
| 21 | 16.17 | 5.4 |
| 58 | 16.49 | 6.8 |
| 136 | 16.81 | 6.2 |
| 95 | 16.87 | 6.9 |
| 125 | 18.01 | 4.4 |
| 97 | 20.17 | 5.9 |
| 25 | 20.36 | 5.2 |
| 96 | 21.24 | 6.2 |
| 40 | 21.38 | 4.7 |
| 73 | 23.49 | 8.0 |
| 8 | 23.83 | 5.7 |
| 127 | 25.26 | 6.9 |
| 189 | 25.43 | 5.5 |
| 57 | 25.77 | 5.4 |
| 222 | 30.35 | 8.0 |
| 93 | 35.31 | 4.8 |
| 9 | 37.92 | 4.5 |
| 61 | 39.04 | 4.5 |
| 229 | 40.09 | 7.1 |
| 87 | 40.23 | 5.0 |
| 120 | 40.60 | 5.9 |
| 20 | 40.63 | 5.9 |
| 11 | 41.42 | 4.6 |
| 81 | 42.14 | 5.4 |
| 137 | 42.23 | 4.6 |
| 219 | 42.69 | 5.8 |
| 56 | 43.01 | 7.2 |
| 114 | 43.01 | 5.9 |
| 167 | 43.01 | 5.5 |
| 13 | 44.13 | 6.7 |
| 107 | 44.13 | 5.8 |
| 217 | 44.13 | 6.9 |
| 221 | 44.13 | 6.5 |
| 224 | 44.13 | 4.9 |
| 42 | 44.34 | 6.3 |
| 43 | 44.34 | 4.4 |
| 131 | 44.45 | 6.9 |
| 29 | 44.46 | 5.9 |
| 78 | 44.76 | 5.8 |
| 55 | 44.77 | 5.1 |
| 88 | 45.40 | 6.8 |
| 100 | 45.40 | 7.1 |
| 34 | 45.66 | 5.1 |
| 170 | 46.19 | 5.6 |
| 171 | 46.19 | 4.3 |
| 163 | 46.51 | 5.9 |
| 129 | 47.31 | 4.7 |
| 132 | 47.31 | 4.4 |
| 194 | 47.31 | 4.9 |
| 199 | 47.47 | 6.5 |
| 7 | 47.54 | 4.6 |
| 207 | 48.05 | 5.2 |
| 149 | 48.50 | 5.1 |
| 202 | 48.98 | 4.8 |
| 130 | 50.32 | 5.3 |
| 143 | 50.39 | 6.9 |
| 70 | 52.35 | 5.8 |
| 144 | 52.46 | 7.0 |
| 157 | 52.46 | 5.6 |
| 49 | 52.85 | 5.4 |
| 50 | 52.85 | 5.0 |
| 53 | 52.94 | 5.1 |
| 54 | 52.94 | 4.1 |
| 112 | 54.15 | 5.5 |
| 123 | 54.75 | 4.2 |
| 124 | 54.75 | 5.3 |
| 153 | 54.77 | 5.3 |
| 106 | 55.55 | 6.2 |
| 126 | 56.96 | 5.2 |
| 148 | 56.96 | 4.9 |
| 186 | 56.96 | 4.5 |
| 173 | 57.85 | 4.7 |
| 187 | 57.85 | 4.0 |
| 122 | 58.16 | 4.8 |
| 74 | 59.00 | 6.5 |
| 89 | 59.06 | 6.4 |
| 90 | 59.06 | 5.3 |
| 128 | 59.56 | 4.0 |
| 133 | 59.56 | 5.1 |
| 145 | 59.56 | 5.3 |
| 146 | 59.56 | 4.8 |
| 139 | 59.76 | 4.1 |
| 140 | 59.76 | 5.8 |
| 158 | 59.76 | 5.3 |
| 223 | 60.56 | 5.7 |
| 161 | 61.16 | 4.0 |
| 198 | 61.16 | 4.3 |
| 210 | 61.16 | 6.1 |
| 211 | 61.16 | 4.1 |
| 150 | 63.44 | 5.7 |
| 155 | 67.45 | 4.9 |
| 166 | 67.45 | 4.1 |
| 200 | 67.47 | 4.9 |
| 209 | 67.47 | 4.0 |
| 177 | 67.65 | 4.0 |
| 178 | 67.65 | 4.5 |
| 154 | 68.95 | 4.9 |
| 1 | n.d. | 7.3 |
| 2 | n.d. | 6.8 |
| 3 | n.d. | 6.7 |
| 4 | n.d. | 5.7 |
| 51 | n.d. | 5.8 |
| 59 | n.d. | 5.1 |
| 60 | n.d. | 5.6 |
| 68 | n.d. | 6.4 |
| 104 | n.d. | 6.6 |
| 105 | n.d. | 6.0 |
| 108 | n.d. | 7.0 |

The invention claimed is:
1. A compound according to the general Formula (Ia) or the general Formula (Ib)

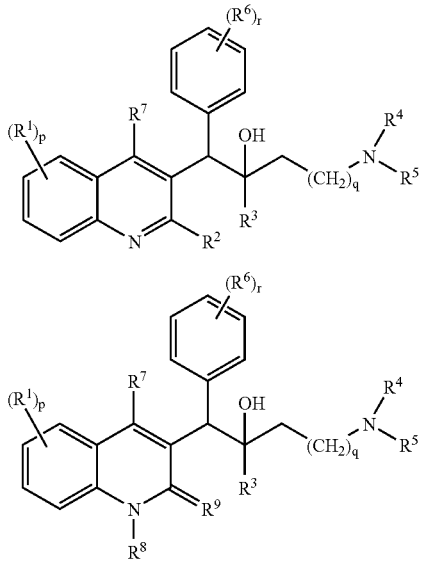

the pharmaceutically acceptable acid or base addition salts thereof, the stereochemically isomeric forms thereof, the tautomeric forms thereof and the N-oxide forms thereof, wherein:

$R^1$ is hydrogen, halo, haloalkyl, cyano, hydroxy, Ar, Het, alkyl, alkyloxy, alkylthio, alkyloxyalkyl, alkylthioalkyl, Ar-alkyl or di(Ar)alkyl;

p is an integer equal to zero, 1, 2, 3 or 4;

$R^2$ is hydrogen, hydroxy, thio, alkyloxy, alkyloxyalkyloxy, alkylthio, mono or di(alkyl)amino or a radical of formula

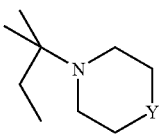

wherein Y is $CH_2$, O, S, NH or N-alkyl;

$R^3$ is alkyl, Ar, Ar-alkyl, Het or Het-alkyl;

q is an integer equal to zero, 1, 2, 3 or 4;

$R^4$ and $R^5$ each independently are hydrogen, alkyl or benzyl; or $R^4$ and $R^5$ together and including the N to which they are attached may form a radical selected from the group of pyrrolidinyl, 2H-pyrrolyl, 2-pyrrolinyl, 3-pyrrolinyl, pyrrolyl, imidazolidinyl, pyrazolidinyl, 2-imidazolinyl, 2-pyrazolinyl, imidazolyl, pyrazolyl, triazolyl, piperidinyl, pyridinyl, piperazinyl, imidazolidinyl, pyridazinyl, pyrimidinyl, pyrazinyl, triazinyl, morpholinyl and thiomorpholinyl, optionally substituted with alkyl, halo, haloalkyl, hydroxy, alkyloxy, amino, mono- or dialkylamino, alkylthio, alkyloxyalkyl, alkylthioalkyl and pyrimidinyl;

$R^6$ is hydrogen, halo, haloalkyl, hydroxy, Ar, alkyl, alkyloxy, alkylthio, alkyloxyalkyl, alkylthioalkyl, Ar-alkyl or di(Ar)alkyl; or two vicinal $R^6$ radicals may be taken together to form a bivalent radical of formula —CH=CH—CH=CH—;

r is an integer equal to 0, 1, 2, 3, 4 or 5; and $R^7$ is hydrogen, alkyl, Ar or Het;

$R^8$ is hydrogen or alkyl $R^9$ is oxo; or $R^8$ and $R^9$ together form the radical =N—CH=CH—.

alkyl is a straight or branched-saturated hydrocarbon radical having from 1 to 6 carbon atoms; or is a cyclic saturated hydrocarbon radical having from 3 to 6 carbon atoms; or is a cyclic saturated hydrocarbon radical having from 3 to 6 carbon atoms attached to a straight or branched saturated hydrocarbon radical having from 1 to 6 carbon atoms; wherein each carbon atom can be optionally substituted with halo, hydroxy, alkyloxy or oxo;

Ar is a homocycle selected from the group of-phenyl, naphthyl, acenaphthyl, tetrahydronaphthyl, each optionally substituted with 1, 2 or 3 substituents, each substituent independently selected from the group of hydroxy, halo, cyano, nitro, amino, mono- or dialkylamino, alkyl, haloalkyl, alkyloxy, haloalkyloxy, carboxyl, alkyloxycarbonyl, aminocarbonyl, morpholinyl and mono- or dialkylaminocarbonyl;

Het is a monocyclic heterocycle selected from the group of N-phenoxypiperidinyl, pyrrolyl, pyrazolyl, imidazolyl, furanyl, thienyl, oxazolyl, isoxazolyl, thiazolyl, isothiazolyl, pyridinyl, pyrimidinyl, pyrazinyl and pyridazinyl; or a bicyclic heterocycle selected from the group of quinolinyl, quinoxalinyl, indolyl, benzimidazolyl, benzoxazolyl, benzisoxazolyl, benzothiazolyl, benzisothiazolyl, benzofuranyl, benzothienyl, 2,3-dihydrobenzo[1,4]dioxinyl or benzo[1,3]dioxolyl; each monocyclic and bicyclic heterocycle may optionally be substituted on a carbon atom with 1, 2 or 3 substituents selected from the group of halo, hydroxy, alkyl or alkyloxy;

halo is a substituent selected from the group of fluoro, chloro, bromo and iodo and haloalkyl is a straight or branched saturated hydrocarbon radical having-from 1 to 6 carbon atoms or a cyclic saturated hydrocarbon radical having from 3 to 6 carbon atoms, wherein one or more carbon atoms are substituted with one or more halo-atoms.

2. A compound according to claim 1, characterized in that $R^1$ is hydrogen, halo, cyano, Ar, Het, alkyl, and alkyloxy p is an integer equal to zero, 1, 2, 3 or 4;

$R^2$ is hydrogen, hydroxy, alkyloxy, alkyloxyalkyloxy, alkylthio or a radical of formula

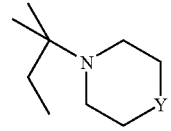

wherein Y is O;

$R^3$ is alkyl, Ar, Ar-alkyl or Het;

q is an integer equal to zero, 1, 2, or 3;

$R^4$ and $R^5$ each independently are hydrogen, alkyl or benzyl; or $R^4$ and $R^5$ together and including the N to which they are attached may form a radical selected from the group of pyrrolidinyl, imidazolyl, triazolyl, piperidinyl, piperazinyl, pyrazinyl, morpholinyl and thiomorpholinyl, optionally substituted with alkyl and pyrimidinyl;

$R^6$ is hydrogen, halo or alkyl; or two vicinal $R^6$ radicals may be taken together to form a bivalent radical of formula —CH=CH—CH=CH—;

r is an integer equal to 1; and $R^7$ is hydrogen;

R[8] is hydrogen or alkyl;
R[9] is oxo; or
R[8] and R[9] together form the radical =N—CH=CH—.
alkyl is a straight or branched saturated hydrocarbon radical having from 1 to 6 carbon atoms; or is a cyclic saturated hydrocarbon radical having from 3 to 6 carbon atoms; or is a cyclic saturated hydrocarbon radical having from 3 to 6 carbon atoms attached to a straight or branched saturated hydrocarbon radical having from 1 to 6 carbon atoms; wherein each carbon atom can be optionally substituted with halo or hydroxy;
Ar is a homocycle selected from the group of phenyl, naphthyl, acenaphthyl, tetrahydronaphthyl, each optionally substituted with 1, 2 or 3 substituents, each substituent independently selected from the group of halo, haloalkyl, cyano, alkyloxy and morpholinyl;
Het is a monocyclic heterocycle selected from the group of N-phenoxypiperidinyl, furanyl, thienyl, pyridinyl, pyrimidinyl; or a bicyclic heterocycle selected from the group of benzothienyl, 2,3-dihydrobenzo[1,4]dioxinyl or benzo[1,3]dioxolyl; each monocyclic and bicyclic heterocycle may optionally be substituted on a carbon atom with 1, 2 or 3 alkyl substituents; and
halo is a substituent selected from the group of fluoro, chloro and bromo.

3. A compound according to claim 1 or 2 wherein R[6] is hydrogen, halo, alkyl.

4. A compound according to any one of claims 1, characterized in that, independently from each other, R[1] is hydrogen, halo, Ar, alkyl or alkyloxy, p=1, R[2] is hydrogen, alkyloxy or alkylthio, R[3] is naphthyl, phenyl or thienyl, each optionally substituted with 1 or 2 substituents selected from the group of halo and haloalkyl, q=0, 1, 2 or 3, R[4] and R[5] each independently are hydrogen or alkyl or R[4] and R[5] together and including the N to which they are attached form a radical selected from the group of imidazolyl, triazolyl, piperidinyl, piperazinyl and thiomorpholinyl, R[6] is hydrogen, alkyl or halo, r is equal to 0 or 1 and R[7] is hydrogen.

5. A compound according to claim 4, characterized in that, independently from each other, R[1] is bromo, R[2] is alkyloxy, R[3] is naphthyl or phenyl, q=1, R[4] and R[5] each independently are hydrogen, methyl or ethyl and R[6] is hydrogen.

6. A compound according to any one of claims 1 wherein the compound is a compound of formula (Ia).

7. A compound according to claim 1, characterized in that the compound is:
1-(6-bromo-2-methoxy-quinolin-3-yl)-2-(3,5-difluoro-phenyl)4-dimethylamino-1-phenyl-butan-2-ol;
1-(6-bromo-2-methoxy-quinolin-3-yl)-4-dimethylamino-2-naphthalen-1-yl-1-phenyl-butan-2-ol;
1-(6-bromo-2-methoxy-quinolin-3-yl)-2-(2,5-difluoro-phenyl)4-dimethylamino-1-phenyl-butan-2-ol;
1-(6-bromo-2-methoxy-quinolin-3-yl)-2-(2,3-difluoro-phenyl)4-dimethylamino-1-phenyl-butan-2-ol;
1-(6-bromo-2-methoxy-quinolin-3-yl)-4-dimethylamino-2-(2-fluoro-phenyl)-1-phenyl-butan-2-ol;
1-(6-bromo-2-methoxy-quinolin-3-yl)-4-dimethylamino-2-naphthalen-1-yl-1-p-tolyl-butan-2-ol;
1-(6-bromo-2-methoxy-quinolin-3-yl)-4-methylamino-2-naphthalen-1-yl-1-phenyl-butan-2-ol; and
1-(6-bromo-2-methoxy-quinolin-3-yl)-4-dimethylamino-2-(3-fluoro-phenyl)-1-phenyl-butan-2-ol,
the pharmaceutically acceptable acid or base addition salts thereof, the stereochemically isomeric forms thereof and the N-oxide forms thereof.

8. A compound according to claim 1 wherein the compound is a compound of Formula (Ia) which can be represented by the following formula

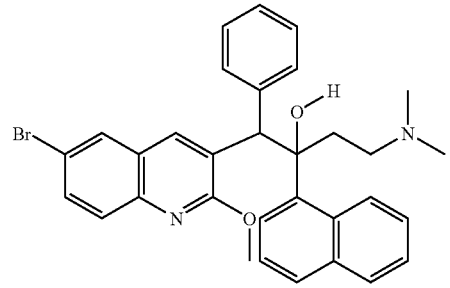

a pharmaceutically acceptable acid or base addition salt thereof or a stereochemically isomeric form thereof.

9. A compound according to claim 8 wherein the compound is the diastereoisomer having a melting point of 210° C., a pharmaceutically acceptable acid or base addition salt thereof or a stereochemically isomeric form thereof.

10. A compound according to claim 8 wherein the compound is the diastereoisomer, which exhibits the highest numerical pIC$_{50}$ value in the M. smegmatis assay relative to the other diastereoisomer B of the same formula, or a pharmaceutically acceptable acid or base addition salt or a stereochemically isomeric form thereof.

11. A compound according to claim 8 wherein the compound is the enantiomeric form which exhibits the lowest numerical MIC value in the M. tuberculosis assay relative to the other enantiomeric forms of the same formula, or a pharmaceutically acceptable acid or base addition salt thereof.

12. A compound according to claim 8 wherein the compound is the enantiomeric form which exhibits the highest numerical pIC$_{50}$ value in the M. smegmatis assay relative to the other enantiomeric forms of the same formula, or a pharmaceutically acceptable acid or base addition salt thereof.

13. A compound according to claim 8 wherein the compound is the enantiomeric form which exhibits a MIC value in the M. tuberculosis assay of less than or equal to 1 microgram/ml, or a pharmaceutically acceptable acid or base addition salt thereof.

14. A compound according to claim 8 wherein the compound is the enantiomeric form which exhibits a pIC$_{50}$ value of greater than 7.5 in the M. smegmatis assay, or a pharmaceutically acceptable acid or base addition salt thereof.

15. A compound according to claim 1 wherein the compound is an enantiomeric form of Formula (Ia) which can be represented by the following formula

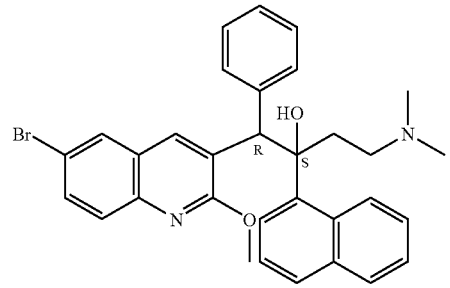

or a pharmaceutically acceptable acid addition salt thereof.

16. A compound according to claim 1 wherein the compound is an enantiomeric form of Formula (Ia) which can be represented by the following formula

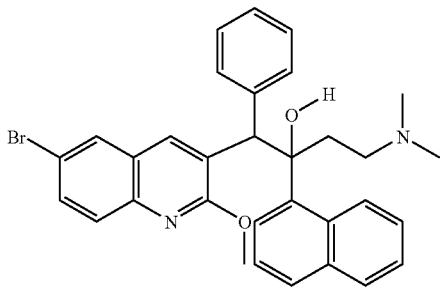

and having the following optical rotation: $[\alpha]_D^{20} = -166.98°$ at a concentration of 0.505 g/100 ml in DMF, or a pharmaceutically acceptable acid or base addition salt thereof.

17. A composition comprising a pharmaceutically acceptable carrier and, as active ingredient, a therapeutically effective amount of a compound as defined in claim 1.

18. Method of treating a patient suffering from a mycobacterial disease, which comprises administering to the patient a therapeutically effective amount of a compound according to claim 1.

19. A process for preparing a compound according to claim 1, characterized in that a compound of Formula (II) is reacted with a compound of Formula (III) according to the following reaction:

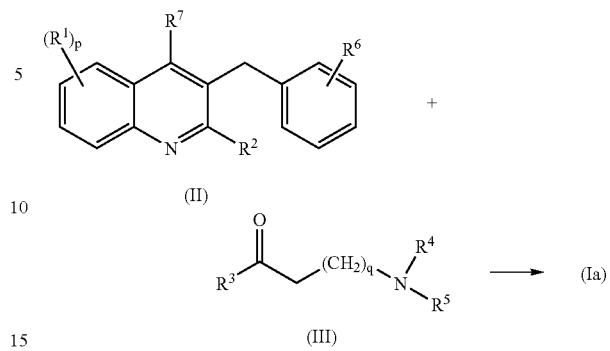

wherein $R^1$, p, $R^2$, $R^3$, q, $R^4$, $R^5$, $R^6$ and $R^7$ are defined in claim 1.

20. A compound according to claim 1 wherein $R^3$ is Ar-alkyl.

21. A compound according to claim 1 wherein q is an integer equal to 3.

22. A compound according to claim 1 wherein alkyl is a straight or branched saturated hydrocarbon radical having from 1 to 6 carbon atoms.

23. A composition comprising a pharmaceutically acceptable carrier and, as an active ingredient, a therapeutically acceptable amount of a compound of claim 15.

24. The method according to claim 18 wherein the mycobacterial disease is tuberculosis.

* * * * *